(12) United States Patent
Gulati et al.

(10) Patent No.: US 7,241,586 B2
(45) Date of Patent: Jul. 10, 2007

(54) POLYPEPTIDE FORMULATIONS AND METHODS FOR MAKING, USING AND CHARACTERIZING THEM

(75) Inventors: Poonam S. Gulati, La Canada, CA (US); Sarnath Chattaraj, Simi Valley, CA (US); Elango S. Minnoor, Northridge, CA (US); Eugene Levin, West Hills, CA (US); Xiao Zhu, Valencia, CA (US); William P. Van Antwerp, Valencia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 8 days.

(21) Appl. No.: 11/060,255

(22) Filed: Feb. 17, 2005

(65) Prior Publication Data

US 2006/0183178 A1 Aug. 17, 2006

(51) Int. Cl.
*C12Q 1/26* (2006.01)
(52) U.S. Cl. ....................................................... 435/25
(58) Field of Classification Search ..................... None
See application file for complete search history.

(56) References Cited

U.S. PATENT DOCUMENTS

| | | | |
|---|---|---|---|
| 4,045,343 A | 8/1977 | Achener et al. | |
| 4,116,837 A | 9/1978 | Biermacher | |
| 4,952,321 A | 8/1990 | Bradshaw et al. | |
| 5,447,556 A | 9/1995 | Pleil et al. | |
| 5,541,097 A * | 7/1996 | Lantero et al. | 435/188 |
| 5,670,054 A | 9/1997 | Kibbey et al. | |
| 5,977,297 A | 11/1999 | Obermeier et al. | |
| 6,090,280 A | 7/2000 | Connelly et al. | |
| 6,122,055 A | 9/2000 | O'Donohue et al. | |
| 6,541,273 B1 | 4/2003 | Plaisance | |
| 6,576,137 B1 | 6/2003 | Ma | |
| 6,602,928 B2 | 8/2003 | Takahashi et al. | |
| 6,679,989 B2 | 1/2004 | Willis et al. | |
| 6,723,236 B2 | 4/2004 | Fisk et al. | |
| 6,759,442 B2 | 7/2004 | Takahashi et al. | |
| 2003/0054979 A1 | 3/2003 | Kim et al. | |
| 2004/0142438 A1 * | 7/2004 | Tonon et al. | 435/177 |

FOREIGN PATENT DOCUMENTS

| | | |
|---|---|---|
| EP | 0 933 430 | 8/1999 |
| WO | WO 2004/0316183 | 4/2001 |

OTHER PUBLICATIONS

Nair L M et al: "Determination of polysorbate 80 in parenteral formulations by high-performance liquid chromatography and evaporative light scattering detection", Journal of Chromatography A., Elsevier, Amsterdam, NL., vol. 1012, No. 1, Sep. 12, 2003, pp. 81-86.
Kibbey T C G et al: "High-performance liquid chromatographic analysis of polydisperse ethoxylated non-ionic surfactants in aqueous samples" Journal of Chromatography A., Elsevier, Amsterdam, NL, vol. 752, No. 1-2, Nov. 1, 1996, pp. 155-165.
Nair L M et al: "Development of a Size-Exclusion Chromarograpy/ELSD Method for the Determination of Poloxamer 188 in a Itraconazole Nanosuspension Formulation" Poster Presented at Pittcon 2004, [Online] Aug. 3, 2004.
C. Guo et al., "Confirmational Structure of Triblock Copolymers by FT-Raman and FTIR Spectroscopy," Journal of Colloid and Interface Science, 1999, 209, pp. 368-373.
Z. Takats et al., "Qualitative and Quantitive Determination of Poloxamer Surfactants By Mass Spectrometry," Rapid Commun. Mass Spectrom., 2001; 15: 805-810.
K. Toel et al., "Extractive Spectrophotometric Determination of Nonionic Surfactants in Water," *Talanta*, vol. 29, pp. 103-106.
J. Peterson et al., "Validation of an HPLC Method for the Determination of Sodium in LY293111 Sodium, a Novel LTC Receptor Anatagonist, Using Evaporative Light Scattering Detection," J. Liquid Chromatography, 1995, 18(2), pp. 331-338.
C. Kumar et al., "Proteins Immobilized at the Galleries of Layered α-Zirconium Phosphate: Structure and Activity Studies," J. Am. Chem. Soc. 2000, 122, 830-837.

* cited by examiner

*Primary Examiner*—Jon Weber
*Assistant Examiner*—Paul Martin
(74) *Attorney, Agent, or Firm*—Gates & Cooper LLP

(57) ABSTRACT

Embodiments of the invention include polypeptide formulations and methods for making, using and characterizing them. Embodiment of the invention include stabilized polypeptide formulations, for example stable glucose oxidase formulations that can be used with glucose sensors used in the management of diabetes. Another embodiment of the invention includes methods to characterize the concentration of nonionic surfactants in stabilized polypeptide formulation for example stable insulin formulations that can be used in the treatment of diabetes.

4 Claims, 6 Drawing Sheets

PRIOR ART

POLYPEPTIDE FORMULATIONS AND METHODS FOR MAKING, USING AND CHARACTERIZING THEM

CROSS REFERENCE TO RELATED APPLICATIONS

This application is related to U.S. patent application Ser. No. 10/989,038, U.S. patent application Ser. No. 10/861,837, and U.S. patent application Ser. No. 10/273,767, the contents of each of which are incorporated herein by reference.

BACKGROUND OF THE INVENTION

1. Field of the Invention

The present invention relates generally to polypeptide formulations such as those used in the treatment and management of diabetes.

2. Description of Related Art

Advancing technologies have made a wide variety of biologically active polypeptides available in sufficiently large quantities for use in both diagnostic as well as therapeutic methodologies. Many polypeptides, however, can lose biological activity by a variety of chemical and physical means including deamidation, aggregation and denaturation. Consequently, the identification and characterization of compositions and methods that can be used to stabilize and/or assess the stability of these agents is essential for the optimization of their benefits.

Stable polypeptide formulations are particularly important for use in devices that expose these agents to elevated temperatures and/or mechanical stress. Stable glucose oxidase formulations, for example, are used with glucose analyte sensors and related devices in the management of diabetes. Similarly, in continuous infusion systems, a fluid containing a therapeutic agent is pumped from a reservoir, usually to a subcutaneous, intravenous, or intraperitoneal depot. Stable insulin formulations, for example are used with continuous infusion systems and related devices in the treatment of diabetes. Formulations of such polypeptides must remain active even though subjected to extended periods of storage prior to use as well as a patient's body heat and motion during use.

SUMMARY OF THE INVENTION

Embodiments of the invention provide polypeptide formulations and methods for making, using and characterizing them.

One embodiment of the invention is a method of determining the concentration of a non-ionic surfactant in an aqueous solution by subjecting the aqueous solution to a chromatographic separation step and then analyzing this solution via evaporative light scattering, such that the concentration of the non-ionic surfactant in the aqueous solution is determined. In certain embodiments of the invention, the non-ionic surfactant is extracted from the aqueous solution and then concentrated prior to the chromatographic separation step. In these methods, the chromatographic separation step can include reverse-phase chromatography. Optionally, this chromatographic separation step includes high pressure liquid chromatography.

A related embodiment of the invention is a method of determining the concentration of a non-ionic surfactant in an aqueous solution by first extracting the non-ionic surfactant from the aqueous solution, concentrating it and then analyzing this concentrated extract via a high performance liquid chromatograph that is coupled to an evaporative light scattering detector so that the concentration of the non-ionic surfactant in the aqueous solution is determined. In certain embodiments of the invention the high performance liquid chromatograph uses a column containing a matrix that separates the components of the aqueous solution based on their polar and/or nonpolar characteristics.

In certain embodiments of these methods for determining the concentration of a non-ionic surfactant in an aqueous solution, the non-ionic surfactant is a poloxamer. Optionally the non-ionic surfactant in the aqueous solution is poloxamer 171, Triton X-100, Triton X-405, Triton BRIJ-35, Tween-20 or Tween-80. The aqueous solution examined by these methods can include a wide variety of other components in addition to the nonionic surfactant. In one embodiment of the invention, the aqueous solution includes a pharmaceutically acceptable composition. Optionally the aqueous solution includes a therapeutic polypeptide such as an insulin. Typically, the concentration of these non-ionic surfactant in the aqueous solution is less than the critical micelle concentration. In certain embodiments of the invention, the concentration of the non-ionic surfactant in the aqueous solution is between about 0.1 and about 100 parts per million (ppm), and optionally is between about 1 and about 20 parts per million (ppm).

Another embodiment of the invention is a highly stable glucose oxidase composition which includes about 90 KU/mL to about 110 KU/mL glucose oxidase, about 0.12% w/v to about 0.15% w/v potassium sorbate and about 0.01 M potassium phosphate buffer. In these embodiments of the invention, the glucose oxidase is stable for at least 6 months in a plastic container. In certain embodiments, the glucose oxidase is present in a concentration of about 100 KU/mL. Typically, the potassium sorbate is present in a concentration of about 0.15% w/v.

A related embodiment of the invention is a method of making a glucose oxidase composition that is stable for at least 6 months in a plastic container by first preparing a dilute glucose oxidase solution and then concentrating this glucose oxidase solution so that the resulting concentrated solution includes glucose oxidase at a concentration of about 90 KU/mL to about 110 KU/mL, potassium sorbate at a concentration of 0.12% w/v to about 0.18% w/v; and potassium phosphate buffer at a concentration of about 0.01 M. In embodiments of the invention, the glucose oxidase solution is typically concentrated by a process including solid phase extraction or by a process including chromatography.

Another related embodiment of the invention is a method of making a glucose sensor apparatus for implantation within a mammal by: providing a base layer; forming a conductive layer on the base layer, where the conductive layer includes a working electrode; forming an analyte sensing layer on the conductive layer using a composition including glucose oxidase having a concentration of about 90 KU/mL to about 110 KU/mL, potassium sorbate having a concentration of about 0.12% w/v to about 0.18% w/v; and a potassium phosphate buffer having a concentration of about 0.01 M; optionally forming a protein layer on the analyte sensing layer; forming an adhesion promoting layer on the analyte sensing layer or the optional protein layer; forming an analyte modulating layer disposed on the adhesion promoting layer, where the analyte modulating layer includes a composition that modulates the diffusion of the analyte therethrough; and then forming a cover layer disposed on at least a portion of the analyte modulating layer, the cover layer including an aperture over at least a portion of the analyte modulating layer. Yet another embodiment of the invention is sensor made by this method.

Other objects, features and advantages of embodiments of the present invention will become apparent to those skilled in the art from the following detailed description. It is to be understood, however, that the detailed description and specific examples, while indicating embodiments of the present invention are given by way of illustration and not limitation. Many changes and modifications within the scope of the present invention may be made without departing from the spirit thereof, and the invention includes all such modifications.

DETAILED DESCRIPTION OF THE INVENTION

Figure 1:
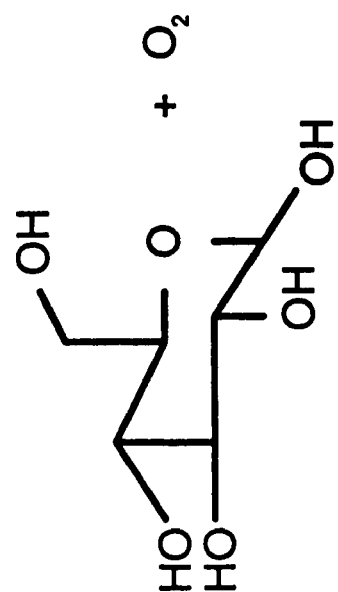
FIG. 1 provides a schematic of the well known reaction between glucose and glucose oxidase. As shown in a stepwise manner, this reaction involves glucose oxidase (GOx), glucose and oxygen in water. In the reductive half of the reaction, two protons and electrons are transferred from β-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In certain electrochemical sensors of the invention, the hydrogen peroxide produced by this reaction is oxidized at the working electrode ($H_2O_2 \rightarrow 2H^+ + O_2 + 2e^-$).
Figure 1:
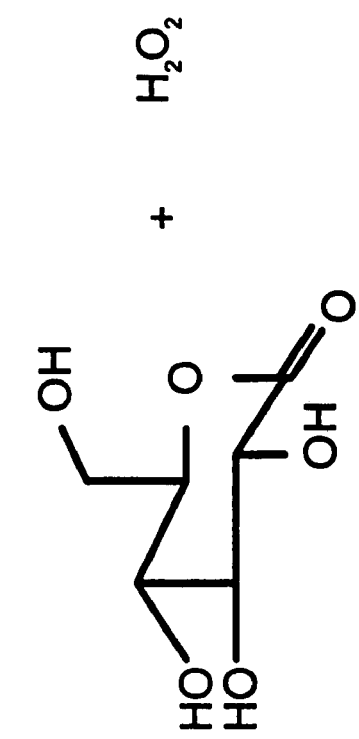

Unless otherwise defined, all terms of art, notations and other scientific terms or terminology used are intended to have the meanings commonly understood by those of skill in the art to which these embodiments of the present invention pertains. In some cases, terms with commonly understood meanings are defined for clarity and/or for ready reference, and the inclusion of such definitions should not necessarily be construed to represent a substantial difference over what is generally understood in the art. Many of the techniques and procedures described or referenced are well understood and commonly employed using conventional methodology by those skilled in the art. As appropriate, procedures involving the use of commercially available kits and reagents are generally carried out in accordance with manufacturer defined protocols and/or parameters unless otherwise noted.

For purposes of the present invention, as disclosed and claimed, the following terms and abbreviations have the following meanings.

The terms "polypeptide" and "protein" are used interchangeably and encompass natural, synthetic and recombinant polypeptides having a desired biological activity (e.g. insulin polypeptides), including polypeptides and proteins having deleted, replaced or altered amino acid sequences in comparison with the full-length natural polypeptide or biologically active fragments thereof.

The term "stability" refers to the physical and chemical stability of formulations of polypeptides such as insulin and its analogs. Physical instability of a protein formulation may be caused by aggregation of the protein molecules to form higher order polymers or even precipitates. A "stable" formulation is one where the degree of aggregation of proteins is acceptably controlled, and does not increase unacceptably with time. In certain embodiments of the invention, a polypeptide formulation is considered stable over a certain time period if the degree of aggregation is within about 1, 2, 3, 4, 5, 10, 15, 20, 25 or 30% of the degree of aggregation observed in the starting material. In certain embodiments of the invention, a polypeptide formulation is considered stable over a certain time period if the polypeptide's biological activity is at least about 99, 95, 90, 85, 80, 75, 70, 65, 60, 55 or 50% of the activity observed with the starting material. Physical stability may be assessed by methods well-known in the art, including measurement of a sample's apparent attenuation of light (absorbance, or optical density). Such a measurement of light attenuation relates to the turbidity of a formulation. Turbidity is produced by aggregation or precipitation of proteins or complexes in the formulation. Other methods for assessing physical stability are well-known in the art.

The terms "monomeric human insulin analog", "monomeric insulin analog" and "human insulin analog" are well-known in the art, and refer generally to fast acting analogs of human insulin, which include: human insulin, where Pro at position B28 is substituted with Asp, Lys, Leu, Val, or Ala, and where position B29 is Lys or is substituted with Pro; AlaB26-human insulin, des(B28-B30) human insulin; and des(B27) human insulin. Such monomeric insulin analogs are disclosed in U.S. Pat. No. 5,514,646, WO 99/64598, WO 99/6459A2 and WO 96/10417A1. The structure of human insulin is disclosed in Nature 187, 483 (1960). A review of the research, development, and recombinant production of human insulin is found in Science 219, 632-637 (1983). See also U.S. Pat. No. 4,652,525 (rat insulin) and U.S. Pat. No. 4,431,740 (human insulin).

The term "administer" means to introduce formulation of the present invention into the body of a patient in need thereof to treat a disease or condition.

The term "continuous infusion system" refers to a device for continuously administering a fluid to a patient parenterally for an extended period of time or for, intermittently administering a fluid to a patient parenterally over an extended period of time without having to establish a new site of administration each time the fluid is administered. The fluid contains a therapeutic agent or agents. The device includes a reservoir for storing the fluid before it is infused, a pump, a catheter, or other tubing for connecting the reservoir to the administration site via the pump, and control elements to regulate the pump. The device may be constructed for implantation, usually subcutaneously. In such a case, the insulin reservoir will usually be adapted for percutaneous refilling. Obviously, when the device is implanted, the contents of the reservoir will be at body temperature, and subject to the patient's body motion.

The term "treating" refers to the management and care of a patient having a pathology such as diabetes or hyperglycemia, or other condition for which insulin (or other polypeptide) administration is indicated for the purpose of combating or alleviating symptoms and complications of those conditions. Treating includes administering a formulation of present invention to prevent the onset of the symptoms or complications, alleviating the symptoms or complications, or eliminating the disease, condition, or disorder.

Certain embodiments of the invention include therapeutic formulations. Therapeutic formulations typically include a carrier. Suitable carriers and their formulations are described in *Remington's Pharmaceutical Sciences,* 16th ed., 1980, Mack Publishing Co., edited by Osol et al. Typically, an appropriate amount of a pharmaceutically-acceptable salt is used in the carrier to render the formulation isotonic. Examples of the carrier include saline, Ringer's solution and dextrose solution. The pH of the carrier is typically from about 5 to about 8, and more typically from about 7.4 to about 7.8. It will be apparent to those persons skilled in the art that certain carriers may be more preferable depending upon, for instance, the route of administration and concentration of active agent being administered. The carrier may be in the form of a lyophilized formulation or aqueous solution. Acceptable carriers, excipients, or stabilizers are typically nontoxic to cells and/or recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; and/or non-ionic/anionic surfactants such as TWEEN™, PLURONICS™ or polyethylene glycol (PEG).

The term "phenolic preservative" typically refers to art accepted phenolic preservatives such as chlorocresol, m-cresol, phenol, or mixtures thereof.

An "isotonicity agent" is a compound that is physiologically tolerated and imparts a suitable tonicity to a formulation to prevent the net flow of water across cell membranes that are in contact with the formulation. Compounds, such as glycerin, are commonly used for such purposes at known concentrations. Other possible isotonicity agents include salts, e.g., sodium chloride, dextrose, and lactose.

Embodiments of the invention are discussed in detail in the following sections.

I. Methods of Determining Nonionic Surfactant Concentrations in Aqueous Polypeptide Formulations Non-ionic surfactants such as poloxamers are often used as excipients in protein based formulations (e.g. therapeutic formulations) where they can impart exceptional stability. For example, Poloxamer 171 can be used as an excipient of insulin formulation (e.g. U400 Human Recombinant Insulin Formulation). In this context, these types of surfactants are typically used at concentrations less than the critical micelle concentration (CMC), often at the part per million level. The concentration of Poloxamer 171 in such formulations is typically present in trace levels (e.g. about 10 parts per million).

The constituents in polypeptide formulations are typically tested during manufacture to, for example, ensure consistency from batch to batch. Because anionic surfactants typically used in these formulations contain no reactive chemical functional group and no chromophores however, their quantitation at such ppm levels can be difficult. Classical methods involve methylene blue color development and precipitation as barium complexes followed by gravimetric quantitation. Unfortunately, the presence of proteins and peptides often interfere with the quantitation of the surfactant.

Embodiments of the present invention provide methods and materials for characterizing the concentration of non-ionic surfactant(s) in these formulations that are designed to prevent the destabilization of biologically active polypeptides. While specific embodiments of the invention are directed to stabilization of insulin and its analogs, polypeptides which are particularly susceptible to denaturation and aggregate formation, the utility of the invention extends generally to all protein and polypeptide pharmaceuticals. Polypeptide formulations suitable for use in the practice of the present invention include, for example, insulin and it analogs (e.g. LysB28ProB29-human insulin and AspB28 human insulin), interleukins (e.g. IL-2 and its analogs), interferons including β-interferon (IFN-β and its analogs such as IFN-$\beta_{ser17}$), as described in EPO 185459B1 (incorporated herein by reference), hGH, and other polypeptides that are prone to destabilization in solution.

Embodiments of the invention provide reliable and specific methods that use evaporative light scattering coupled to chromatography as a way to quantify ppm levels of non-ionic surfactants. The methods can be used for example to determine the concentrations of these compounds in the presence of therapeutic proteins. In an illustrative embodiment, this method can include an extraction process, followed by High Performance Liquid Chromatographic and evaporative light scattering for determination the Poloxamer 171 content of an aqueous solution. Example 1 below provides an illustrative procedure for the quantification of ppm levels of poloxamer 171 in an insulin formulation as an example. Example 2 below shows that the method used for the determination of poloxamer 171 in Example 1 can be used for the analysis of a wide variety of non-ionic surfactants.

One group of nonionic surfactants that can be analyzed by embodiments of the invention is poloxamers. Poloxamers are widely used as surfactants, emulsifying agents and pharmaceutical excipients. Some poloxamers are used as protein stabilizers (see, e.g. Izutsu et al., Pharm. Res. 12, 1995, 838-843), coating agents (see, e.g. De Jaeghere et al., Mathiowitz, E. (Ed.), Encyclopedia of Controlled Drug Delivery, vol. 2. Wiley, New York, 1999, 641 664; and De Jaeghere et al., Proc. Int. Symp. Control. Rel. Bioact. Mater. 26, 1999, 709-710) steric stabilizers of nanosphere systems (see, e.g. Mehnert et al., Adv. Drug Del. Rev. 47, 2001, 165-196), sensitizers for multidrug-resistant cells (see, e.g. Kabanov A V, Alakhov Crit Rev Ther Drug Carrier Syst. 2002;19(1):1-72) and as immunoadjuvants (see, e.g. R. Bomford, Immunology 44, 1981, 187-192; R. Hunter et al., J. Immunol. 127 1981, 1244-1250; R. L. Hunter et al., J. Immunol. 133, 1984, 3167-3175; R. L. Hunter et al., Scand. J. Immunol. 23, 1986, 287-300; R. Hunter et al., Vaccine 9, 1991, 250-256; R. L. Hunter et al., AIDS Res. Hum. Retroviruses 10, 1994, pp. S95-S98; A. C. Allison et al., J. Immunol. Methods 95, 1986, 157-168; A. C. Allison et al., Semin. Immunol. 2, 1990, 369-374; N. E. Byars et al., Vaccine 5, 1987, 223-228; Y. Ke et al., Cell Immunol. 176, 1997, 113-121; P. Millet et al., Vaccine 10, 1992, 547-550; and K. Takayama et al., Vaccine 9, 1991, 257-265). They are also added to insulin formulations to prevent the adsorption of insulin to hydrophobic surfaces and to reduce the aggregation of insulin thereby increasing the long-term stability of insulin (see, e.g. Thurow H, Geisen K., Diabetologia, 27 (2), 1984, 212-8; and Walter H M et al., Diabetes Res, 13(2), 1990, 75-7).

Detection and chemical characterization of poloxamers using static secondary ion mass spectrometry (SSIMS) (see, e.g. D. Briggs, A. Brown, J. C. Vickerman, Handbook of Secondary Ion Mass Spectrometry, Wiley, New York, 1989), X-ray photoelectron spectroscopy (XPS) (see, e.g. P. D. Scholes et al., Journal of Controlled Release, Volume 59, Issue 3, 2 Jun. 1999, 261-278), gel permeation chromatography (see, e.g. Q. Wang et al., Eur. Polym. J., Vol. 29, No. 5, 1.993, 665-669), size exclusion chromatography (see, e.g. B. Erlandsson et al., Journal of Pharmaceutical and Biomedical Analysis, 31, 2003, 845-858), FT-Raman and FTIR spectroscopy have been described elsewhere (see, e.g. Confirmational structure of triblock copolymers by FT-Raman and FTIR spectroscopy, Journal of Colloid and Interface Science, 209, 1999, 368-373). Takats et al. have reported a mass spectrometry method to analyze poloxamers (see, e.g. Z. Takats et al., Rapid Commun. Mass Spectrum, 15, 2001, 805-810). Colorimetric method that suffers from interferences has been reported (see, e.g. B. M. Milwidsky, Detergent analysis: a handbook for cost-effective quality control, George Godwin, London, 1982, 100). Non-ionic surfactants and their metabolites have been analyzed using Lc-ms (see, e.g. Antonio Di Corcia, Journal of Chromatography A, Volume 794, Issues 1-2, 23, 1998, 165-185; and K. Levsen et al., Journal of Chromatography A, Volume 323, Issue 1, 17, 1985, 135-141), liquid chromatography-fluorescence (see, e.g. M. Zanette et al., Journal of Chromatography A, 756, 1996, 159-174), tensammetric (A. Szymanski et al., Analyst, 121, 1996, 1897-1901) and spectrophotometry (see, e.g. Toel et al., Talanta, Vol. 29, 1982, 103-106; and N. H. Anderson et al., Analyst, Vol. 107, 1982, 836-838).

The analysis methods that have been published for poloxamers and non-ionic surfactants either suffer from interference or need elaborate and expensive instrumentation. Embodiments of the invention avoid these difficulties by using a simple extraction method combined with HPLC coupled to an evaporative light-scattering detector. The invention has a number of embodiments. One embodiment is a method of determining the concentration of a non-ionic surfactant in an aqueous solution by first subjecting the aqueous solution to a chromatographic separation step; and then analyzing this aqueous solution via evaporative light scattering in a manner that allows the concentration of the non-ionic surfactant in the aqueous solution to be determined. The term surfactant refers to a substance capable of reducing the surface tension of a liquid in which it is dissolved and the term "nonionic" (anionic) refers to the class of compounds in which the molecules do not ionize in aqueous solutions. A chromatographic separation step is defined as a separation step sufficient to separate nonionic surfactants within a formulation to the degree necessary to perform evaporative light scattering in order to determine the concentration of the nonionic surfactant. In embodiments of the invention, the chromatographic separation step involves the separation of a mixture of compounds in the aqueous solution into their individual components by passing a fluid along or through a stationary phase. In such separation steps, certain components of the mixture in the fluid tend to adsorb or dissolve onto the stationary phase differently than one another. As a result, some components move at different rates depending on their interaction with the stationary phase.

In certain embodiments of the invention, the non-ionic surfactant is extracted from the aqueous solution and then concentrated prior to the chromatographic separation step. An illustrative embodiment of the invention is a method of determining the concentration of a non-ionic surfactant in an aqueous solution by extracting the non-ionic surfactant from the aqueous solution, concentrating this extract and then analyzing the concentrated non-ionic surfactant via high performance liquid chromatography coupled to an evaporative light scattering detector so that the concentration of the non-ionic surfactant in the aqueous solution is determined. In these methods, the chromatographic separation step can include reverse-phase chromatography. In certain embodiments of the invention the high performance liquid chromatograph uses a column matrix that separates the components of the aqueous solution based on their polar and/or nonpolar characteristics. Optionally such a matrix utilizes C8 chemistry. Embodiments of the invention can be used to examine the concentration of nonionic surfactants in a wide variety of different formulations. In one embodiment, the aqueous solution is a pharmaceutically acceptable composition. In another embodiment of the invention, the aqueous solution includes a therapeutic polypeptide, for example insulin.

Embodiments of the invention utilize high-pressure or high-performance liquid chromatography in the selective isolation of the compound of interest. Liquid chromatography is a method using two phases, solid and liquid, in contact with one another. The typical liquid chromatography system consists of five basic parts: solvent pump(s), injector(s), column(s) (stationary phase), detector(s), and recorder(s) (computer). High-pressure or high-performance liquid chromatography is one well known and versatile type of chromatography (see, e.g. U.S. Pat. Nos. 4,045,343 4,116,837 5,977,297 and 6,679,989).

Embodiments of the invention utilize evaporative light scattering. Evaporative light scattering detectors (ELSD) are highly sensitive liquid chromatography detectors for non-volatile solutes dissolved in a volatile liquid stream (solvent). An ELSD typically operates in three stages. First nebulisation of the solvent occurs where the solvent or solvent/solute solution is atomised into a dispersion of droplets by a venturi jet operated by a jet of compressed air or an inert gas, such as nitrogen. Secondly the atomised spray passes into an evaporation chamber under the influence of the nebuliser gas flow, which may be fan assisted, that directs the atomised spray down the evaporation chamber and vents the exhaust at the rear of the instrument. The third stage is that of detection. Collimated light is passed through the instrument perpendicularly to the direction of gas flow at the base of the evaporation chamber. A light trap is positioned opposite the light source to eliminate internal reflections inside the body of the instrument. When a pure solvent is evaporated only its vapor passes through the light path and the amount of light scattered is small and constant. The presence of a non-volatile solute causes a particle cloud to pass through the light path resulting in light scattering. The scattered light generates a signal response from a photomultiplier or other light sensitive device, which is provided in the detection system. The quantity of light detected is dependent on both concentration and particle size distribution of the solute.

Evaporative light scattering detector (ELSD) may be advantageously used in conjunction with high performance liquid chromatography (HPLC) to quantitate compounds. Unlike UV absorbance detectors, the response of the ELSD is not dependent on the presence of a chromophore in the analyzed compound. Chromophores vary from compound to compound, and the UV absorbance detector responds differently to different chromophores. As such, a large number of standards are disadvantageously required when using a UV absorbance detector for analyzing a large number and variety of compounds. Moreover, chromophores may be absent in many of the compounds present in chemical libraries, frustrating the detection of such compounds via UV absorbance. For additional background concerning the shortcomings of previously described analytical techniques, see U.S. Pat. No. 5,670,054, incorporated by reference herein. Additional information pertaining to ELSD, can be found in U.S. Pat. Nos. 5,670,054, 6,090,280 and 6,122,055 as well as Peterson et al., "Validation of an HPLC Method for the Determination of Sodium in LY293111 Sodium, a Novel LTC Receptor Antagonist, Using Evaporative Light Scattering Detection," J. Liquid Chromatography, 18(2), pp. 331-338 (1995).

In certain embodiments of the invention, the concentration of the non-ionic surfactant in the aqueous solution is less than the critical micelle concentration. In related embodiments of the invention, the concentration of the non-ionic surfactant in the aqueous solution is between about 0.1 and about 100 parts per million (ppm) and optionally is between about 1 and about 20 parts per million (ppm). The critical micelle concentration is the concentration at which micelles begin to form in a system including solvent(s), surfactant(s), possibly other solutes and a defined physical environment. The critical micelle concentration (CMC) can be approximately defined as the lipid monomer concentration at which appreciable amounts (>5% of total) of micellar aggregates first begin to appear in the equilibrium:

$$nM_1 <=> M_n$$

Micelles are distinct groups of monomers that occur when enough monomers are available to saturate the solution, in this case water, they coalesce to form the micelle. At this point, (critical micelle concentration), the monomer concentration reaches equilibrium, and as more surfactant is added, these additional monomers form micelle. This critical concentration is easily measured by any of the well known methods, the most common being the change in surface tension of the liquid that the surfactant is being dissolved in. So in effect, by the simple process of surface tension measurement, one can determine if there are monomers or micelles present in the solution. A common practice and mechanism of cleaning or dispensing chemical compositions with surfactants is to use surfactants at a concentration in use dilution that is higher than the critical micelle concentration for the surfactant of choice. This is because the micelles have the capability in this state to solubilize, emulsify, and dislodge soils in cleaning for removal and rinsing away. At less than the critical micelle concentration it has been long established that the surfactant molecules exist only as monomers, (that is as free independent units), and can actually have a negative effect upon cleaning.

In certain embodiments of the invention, the non-ionic surfactant in the formulation is a poloxamer. The term "poloxamer" is used according to its art accepted meaning and refers to any of a series of nonionic surfactants of the polyoxypropylene-polyoxyethylene copolymer type, having the general formula $HO(C_2H_4O)_a(C_3H_6O)_b$-$(C_2H_4O)_cH$, where a=c; the molecular weights of the members of the series vary from about 1000 to more than 16,000. The term is used in conjunction with a numerical suffix for individual unique identification of products that may be used as a food, drug, or cosmetic. Poloxamers may be surfactants, emulsifiers, or stabilizers. In one such illustrative embodiment, the poloxamer is poloxamer 171.

In certain embodiments of the invention, the nonionic surfactant belongs to the TRITON™ X group of surfactants. TRITON™ X surfactants are versatile nonionic surfactants recognized for their wetting, detergency, superior hard surface, metal cleaning and excellent emulsification performance. In one illustrative embodiment, the nonionic surfactant is Triton X-405, also known as 4-Octylphenol polyethoxylate, Poly(oxy-1,2-ethanediyl), alpha-(4-octylphenyl)-omega-hydroxy. In another illustrative embodiment, the nonionic surfactant is Triton BRIJ-35, also known as Polyoxyethylene monolauryl ether. Brij-35 (Polyoxyethyleneglycol dodecyl ether) is a commonly used detergent in HPLC applications. In another illustrative embodiment, the nonionic surfactant is Triton X-100 which is also known as alkylaryl polyether alcohol; Octyl phenol ethoxylate; Polyoxyethylated octyl phenol; alpha-[4-(1,1,3,3-tetramethylbutyl)phenyl]-omega-hydroxypoly(oxy-1,2-ethanediyl); Octoxinol; Triton X 100; Triton X 102; Ethylene glycol octyl phenyl ether; Polyoxyethylene octyl phenyl ether; p-(1,1,3,3-Tetramethylbutyl)phenol ethoxylate; Octylphenoxypolyethoxyethanol; Polyethylene glycol mono [4-(1,1, 3,3-tetramethylbutyl)phenyl]ether; Poly(oxyethylene)-p-tert-octylphenyl ether; POE octylphenol; polyoxyethylene (10) octylphenol; POE (10) octylphenol; POE(10) Octyl Phenyl Ether; Octoxynol-10; POE(3) Octyl Phenyl Ether; Octoxynol-3; POE(30) Octyl Phenyl Ether; Octoxynol-30. The formula for Triton X-100 is $C_{14}H_{22}O(C_2H_4O)_n$ where the average number of ethylene oxide units per molecule is around 9 or 10. In certain embodiments of the invention, the nonionic surfactant belongs to the Tween Series surfactants. In one such embodiment, the nonionic surfactant is Tween-20 ($C_{58}H_{114}O_{26}$), also known as sorbitan mono-9octadecenoate poly(oxy-1,1-ethanedlyl), polyoxyethylene sorbitan monolaurate, poly(oxyethylene) sorbitan monolaurate, polyoxyethylene (20) sorbitan monolaurate, Poe 20 sorbitan monolaurate, PSML, armotan pml-20, capmul, emsorb 6915, glycospere L-20 or liposorb L-20. In another such embodiment, the nonionic surfactant is Tween-80, also known as polyethylene 20 sorbitan monooleate.

Embodiments of the present invention include formulations designed to address problems in the art related to the destabilization of polypeptides, a phenomena which can be measured by a number of procedures known in the art. For example, a typically unstable polypeptide is IL-2, which destabilizes via at least three pathways: aggregation, methionine oxidation, and deamidation (Kenney et al., "Parameters for the evaluation of IL-2 stability", Lymphokine Research (1986), 5, S23-S27). Several analytical methods are available to monitor IL-2 changes due to physical and chemical destabilizations during storage. A RP-HPLC method (see e.g. Kunitani et al., "Reversed-Phase chromatography of Interleukin-2 muteins", J. of Chromatography, (1986) 359, 391-402), which applies an acetonitrile gradient to elute IL-2 species from a C4 column, is suitable for such analysis. It detects the main IL-2 species as peak B, a methionine oxidative species (mainly oxidized Met-104) as peak A, a deamidated species (probably Asn 88) as peak B' and other unknown species eluting either earlier or later than these peaks. A native SEC-HPLC has also been developed for monomeric IL-2 using isocratic elution with 200 mM ammonium sulfate and a TosoHaas TSK G2000 column. IL-2 elutes as a single species. In addition, a variety of in vitro bioassays can be used to can be used to determine the bioactivity of a molecule such as insulin or IL-2 (e.g. using HT-2 cell proliferation and MTT stain can be used to determine IL-2 bioactivity, Gillis et. al., J. Immuno. 120, 2027-2032 (1978); Watson, J. Exp. Med., 150, 1510-1519 (1979)). Insulin stability can be measured by any of the various techniques described in the art (see, e.g. U.S. Pat. No. 6,737,401).

The described methods and materials for examining polypeptide formulations can be used to examine formulations containing a variety of buffering compounds such as acetate, phosphate and citrate buffer compounds. For example, formulations examined by these methods can include a buffering system such as one of the buffer systems are well known in the art (e.g. TRIS, HEPES, MOPS, PIPES, MES, MOPSO, TAPSO, POPSO, DIPSO, HEPPSO, CAPSO, AMPSO etc.). In this context, the skilled artisan understands that buffering molecules having like properties can be substituted in circumstances where an equivalent buffering milieu is generated.

The described methods and materials for examining polypeptide formulations can be used to examine formulations containing a variety of other commonly used compounds, for example zinc and a phenolic preservative which are commonly used stabilize polypeptides such as insulin. Both zinc and a phenolic preservative are used to achieve a complex that is stable and capable of rapid dissociation and onset of action. The hexamer complex consists of two zinc ions per hexamer of human insulin analog, and at least three molecules of a phenolic preservative selected from the group consisting of chlorocresol, m-cresol, phenol, and mixtures thereof. Soluble monomeric insulin analog is converted to the hexamer complex by dissolving the monomeric insulin analog in a diluent containing the phenolic preservative in suitable quantities at a pH of about 7 to about 8 and then adding zinc. Zinc is typically added as a zinc salt, such as, without limitation, zinc acetate, zinc bromide, zinc chloride, zinc fluoride, zinc iodide, and zinc sulfate. The skilled artisan will recognize that there are many other zinc salts which also might be used to make the monomeric insulin analog complexes that are part of the present invention. Typically, zinc acetate, zinc oxide, or zinc chloride is used because these compounds do not add new chemical ions to commercially accepted processes.

The formulations can also include isotonicity agents such as glycerol or glycerin. The concentration of glycerin, when it is used, is in the range known in the art for insulin formulations, for example about 16 mg/ml. Methionine can also be included in the disclosed pharmaceutical formulations as a means to effectively inhibit the oxidation of methionine residues in the protein. In addition, nonionic surfactants such as polysorbate 80 may be included to inhibit the damage to polypeptides that can occur with freeze-thawing and mechanical shearing. Moreover, EDTA and other known scavengers of metal ions (which are known to catalyze many oxidation reactions), may be added to further stabilize the compositions. Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) may optionally be added to the formulation.

Insulin and insulin analogs used in embodiment of the present invention can be prepared by any of a variety of recognized techniques including classical solution methods, solid phase methods, semi-synthetic methods, and recombinant DNA methods. Chance, et al., U.S. Pat. No. 5,514,646, issued May 7, 1996, discloses the preparation of various monomeric insulin analogs with sufficient detail to enable one skilled in the art to prepare a variety of analogs. Dissolution of the monomeric insulin analog may be aided by what is commonly known as "acid dissolution." For acid dissolution, the pH the aqueous solvent is lowered to about 3.0 to 3.5 with a physiologically tolerated acid, typically HCl, to aid in the dissolution of the monomeric analog. Other physiologically tolerated acids include, without limitation, acetic acid, citric acid, and sulfuric acid. Phosphoric acid is typically not used to adjust pH in preparing the formulations of the present invention. The pH is then adjusted with a physiologically tolerated base, typically sodium hydroxide, to about pH 7.3 to 7.5. Other physiologically tolerated bases include, without limitation, potassium hydroxide and ammonium hydroxide. Thereafter, the phenolic preservative and zinc are added.

Parenteral formulation embodiments of the present invention can be prepared using conventional dissolution and mixing procedures. To prepare a suitable formulation, for example, a measured amount of monomeric insulin analog in water is combined with the desired preservative, a zinc compound, and the buffering agent, in water in sufficient quantities to prepare the hexamer complex. The formulation is generally sterile filtered prior to administration. Variations of this process would be recognized by one of ordinary skill in the art. For example, the order the components are added, the order in which pH is adjusted, if any, the temperature and ionic strength at which the formulation is prepared, may be optimized for the concentration and means of administration used.

II. Stabilized Formulations of Glucose Oxidase

Embodiments of the invention include glucose oxidase formulations for use in analyte sensing devices such as glucose sensors. In this context, compositions having high concentrations of glucose oxidase (e.g. 100 Kilo units/mL) with enhanced stability properties are highly desirable for use in the manufacture of implantable sensors. The concentrated glucose oxidase solution formulations of the invention exhibit a highly desirable stability profile that makes them well suited for use in the manufacture of implantable sensors. In these formations, the stability enhancer is potassium sorbate. When diluted, the glucose oxidase formulations can be used in the manufacture of External (SubQ) sensors.

A typical formulation of the invention includes: Glucose Oxidase at about 100 KU/mL, potassium sorbate at about 0.15% w/v, in an about 0.01 M potassium phosphate buffer. In certain methods of making this formulation, a dilute solution of glucose oxidase is first prepared. The solution is then concentrated using either solid phase extraction or chromatography. Surprisingly, formulations having this specific combination of constituents are stable for a minimum of 6 months in a plastic vial. These formulations have been found compatible for use in the manufacture of Implantable and SubQ Sensors. Glucose oxidase is used in glucose sensors to catalyze glucose in blood and generate hydrogen peroxide, which is then measured electrically. The major impurity, Catalase, remains at a minimum in this formulation. Catalase can be a competitor for enzymatic activity (with glucose oxidase) when present in a sensor. As is known in the art glucose oxidase can be purchased commercially (e.g. in powder form from suppliers such as Sigma or ICN etc.) or can be manufactured according to art accepted methods (e.g. as described in U.S. Pat. Nos. 3,930,953, 5,094,951 and 5,270,194). The stability of a glucose oxidase formulation can measured by determining analytical attributes in the formulation under specific conditions, such as at a particular temperature and humidity condition over a certain period of time. The analytical attributes that can be measured include glucose oxidase activity, protein content, catalase content, sorbate content, activity loss on heat and physical appearance. The results can then be monitored and compared against pre-specified parameters.

The invention has a number of embodiments. One embodiment is a formulation including glucose oxidase, where the glucose oxidase is present in a concentration of about 90 KU/mL to about 110 KU/mL; potassium sorbate, where the potassium sorbate is present in a concentration of about 0.12% w/v to about 0.18% w/v; and a potassium phosphate buffer; where the potassium phosphate buffer is present in a concentration of about 0.01 M. Unexpectedly, formulations having this specific combination of constituents are stable for a minimum of 6 months in a plastic vial. The term "about" when used to refer to the concentrations of glucose oxidase and potassium sorbate in these formulations is defined as a defined range of 5% of the specifically articulated values. For example, about 0.15% w/v potassium sorbate refers to 0.1455% to 0.1575% w/v potassium sorbate. Embodiments of the invention include those where the glucose oxidase is present in a concentration of about 100 KU/mL. Embodiments of the invention include those where the potassium sorbate is present in a concentration of about 0.15% w/v. Embodiments of the invention include those where the potassium phosphate buffer is present in a concentration of about 0.01 M. In typical embodiments of the invention, the glucose oxidase in the formulation is stable for at least 6 months in a plastic container.

Another embodiment of the invention is a method of making a glucose oxidase composition that is stable for at least 6 months in a plastic container, the method including preparing a glucose oxidase solution; and then concentrating this glucose oxidase solution to produce a glucose oxidase solution that includes glucose oxidase having a concentration of about 90 KU/mL to about 110 KU/mL, potassium sorbate having a concentration of about 0.12% w/v to about 0.18% w/v; and a potassium phosphate buffer having a concentration of about 0.01 M.

Typically, the glucose oxidase solution is concentrated by a process including solid phase extraction and/or by a process including chromatography. As is known in the art, Solid Phase Extraction (SPE) is a sample preparation technique that can be used to clean up and/or concentrates samples before analysis. Compared to liquid-liquid extraction, SPE is typically faster, uses less solvent, eliminates emulsions, and saves money. SPE provides clean extracts and high recoveries. SPE products are typically used one of two ways. The simplest method involves passing the sample through an SPE packed bed that retains interfering sample components while passing the analytes through. The second method passes the sample through an SPE packed bed that retains the analytes and possibly interfering sample components. Interfering components are washed off the packed bed and then the analytes are eluted. Elution can be done with a small volume of solvent to concentrate the sample, increasing detection limits and simplifying the analysis. Illustrative SPE techniques are described for example in U.S. Pat. Nos. 6,759,442, 6,723,236, 6,602,928 and 6,541,273. A variety of chromatographic concentration techniques (e.g. using ion exchange resins) are also known in the art. Illustrative techniques are described for example in U.S. Pat. Nos. 6,576,137 5,447,556 and 4,952,321

Yet another embodiment of the invention is a method of making a glucose sensor apparatus for implantation within a mammal including the steps of: providing a base layer; forming a conductive layer on the base layer, where the conductive layer includes a working electrode; forming an analyte sensing layer on the conductive layer using a composition including glucose oxidase having a concentration of about 90 KU/mL to about 110 KU/mL, potassium sorbate having a concentration of about 0.12% w/v to about 0.18% w/v; and a potassium phosphate buffer having a concentration of about 0.01 M; optionally forming a protein layer on the analyte sensing layer; forming an adhesion promoting layer on the analyte sensing layer or the optional protein layer; forming an analyte modulating layer disposed on the adhesion promoting layer, where the analyte modulating layer includes a composition that modulates the diffusion of the analyte therethrough; and forming a cover layer disposed on at least a portion of the analyte modulating layer, where the cover layer further includes an aperture over at least a portion of the analyte modulating layer. Another embodiment of the invention is a sensor made by this method.

As noted above, embodiments of the invention can be used with sensors of the type used, for example, in subcutaneous or transcutaneous monitoring of blood glucose levels in a diabetic patient. The disclosure further provides methods for making and using such sensors having such formulations. The analyte sensor elements, architectures and methods for making and using these elements can be used to establish a variety of layered sensor structures. Such sensors of the invention exhibit a surprising degree of flexibility and versatility, characteristic which allow a wide variety of sensor configurations to be designed to examine a wide variety of analyte species. In typical embodiments of the present invention, the transduction of the analyte concentration into a processable signal is by electrochemical means. These transducers may include any of a wide variety of amperometric, potentiometric, or conductimetric base sensors known in the art. Moreover, the microfabrication sensor techniques and materials of the instant invention may be applied to other types of transducers (e.g., acoustic wave sensing devices, thermistors, gas-sensing electrodes, field-effect transistors, optical and evanescent field wave guides, and the like) fabricated in a substantially nonplanar, or alternatively, a substantially planar manner. A useful discussion and tabulation of transducers which may be exploited in a biosensor as well as the kinds of analytical applications in which each type of transducer or biosensor, in general, may be utilized is found in an article by Christopher R. Lowe in Trends in Biotech. 1984, 2(3), 59-65.

Specific aspects and uses of the invention are discussed in detail in the following sections.

Figure 2:
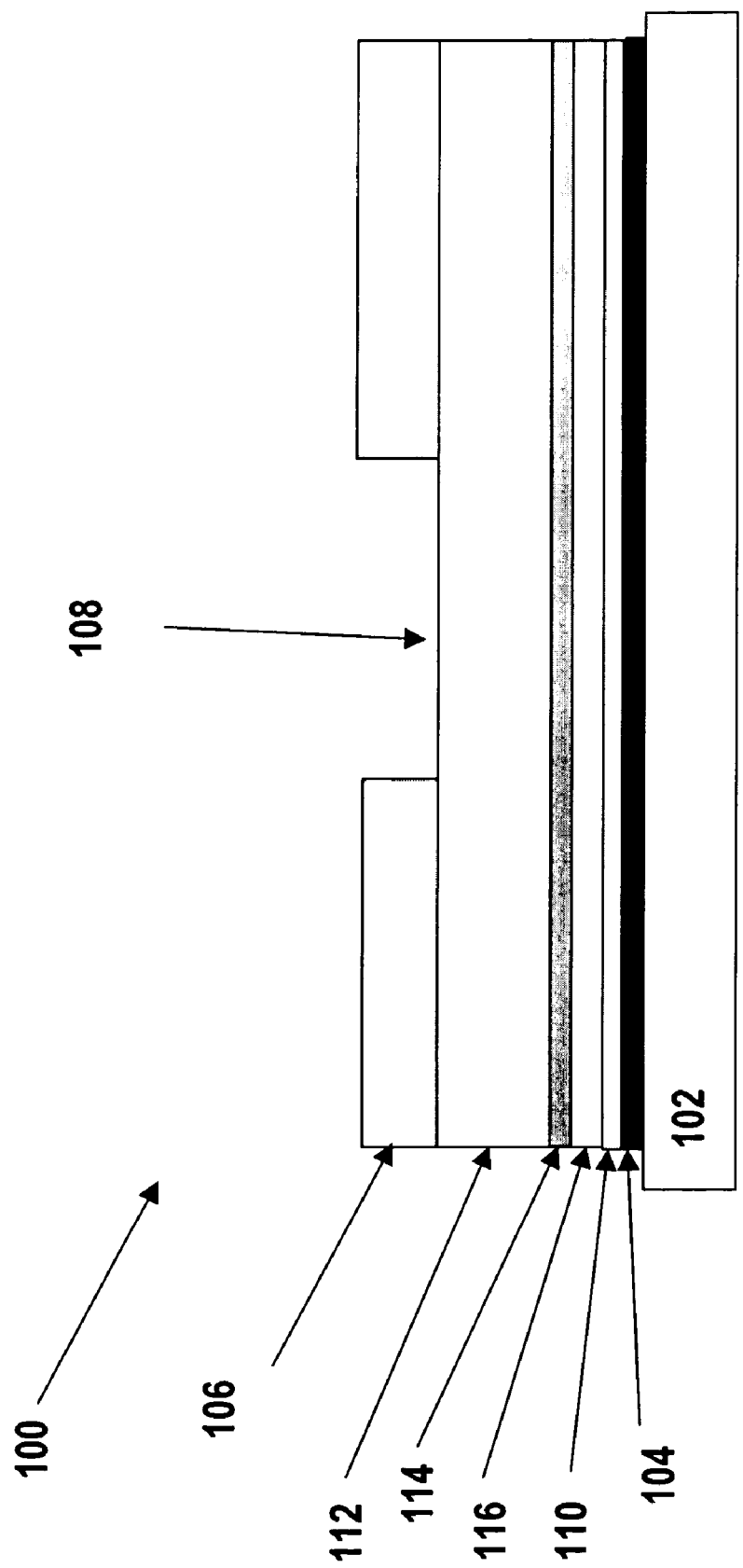
FIG. 2 provides a diagrammatic view of a typical analyte sensor configuration.
Figure 3:
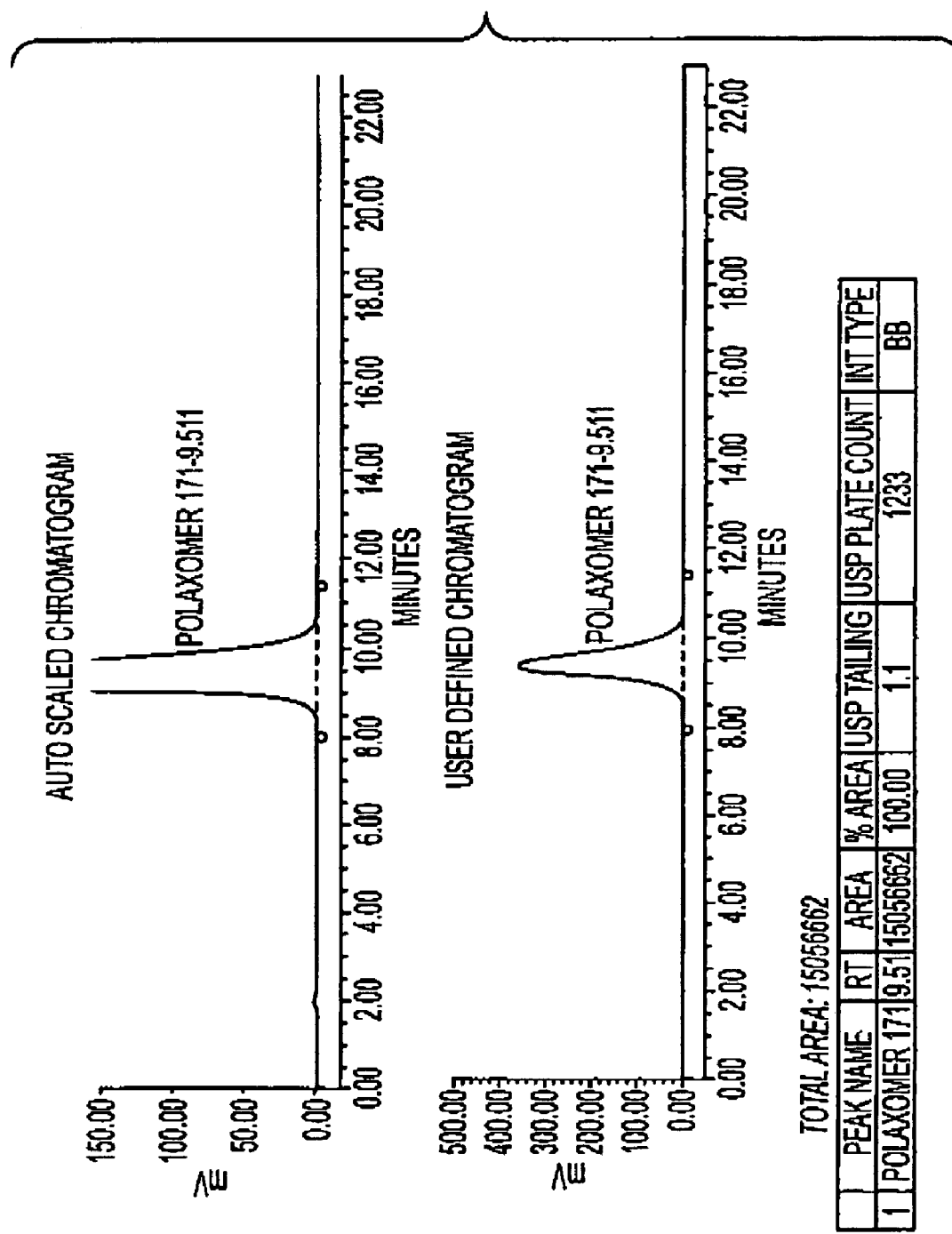
FIG. 3 shows data that is typical of a system suitability chromatogram.
Figure 4:
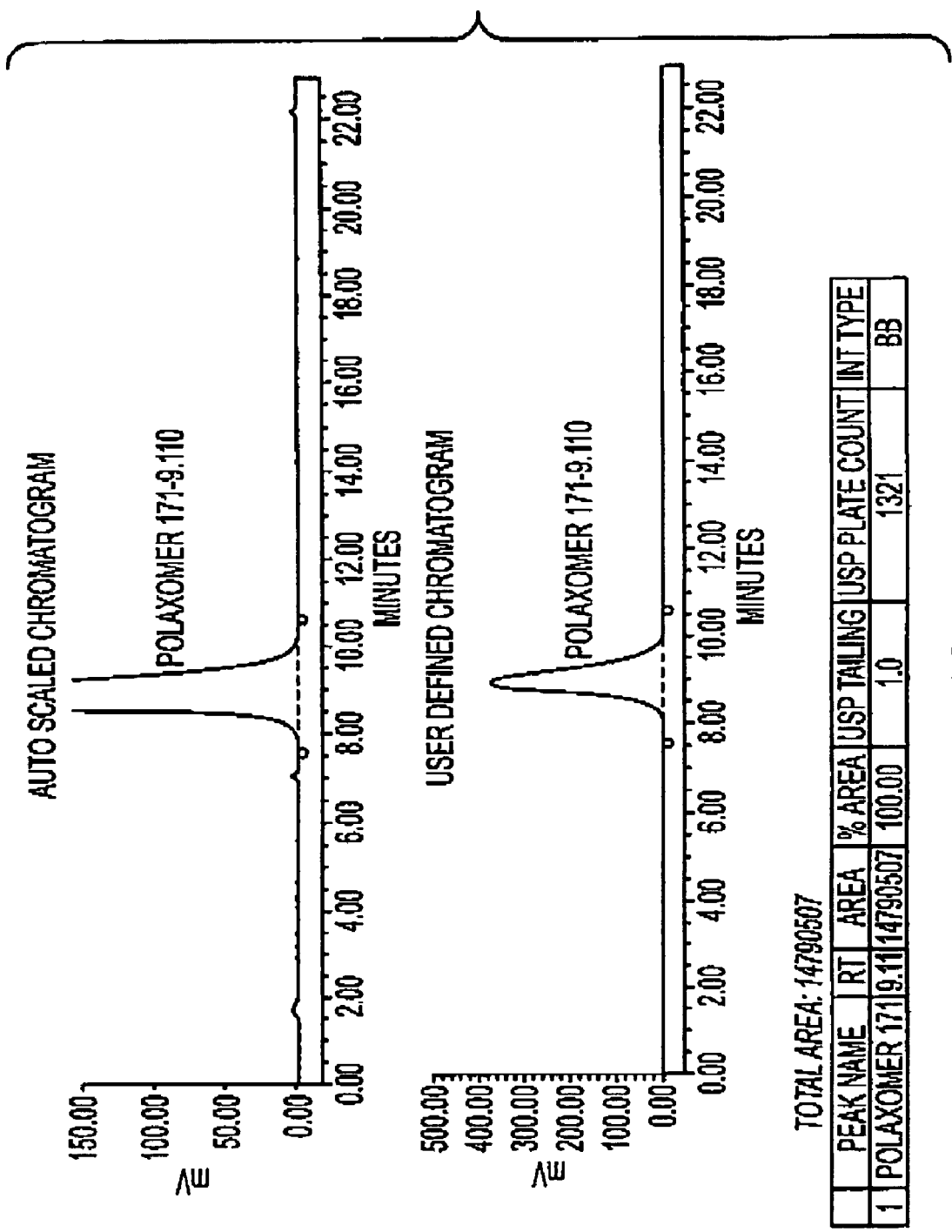
FIG. 4 shows a representative chromatogram of a reference standard.
Figure 5:
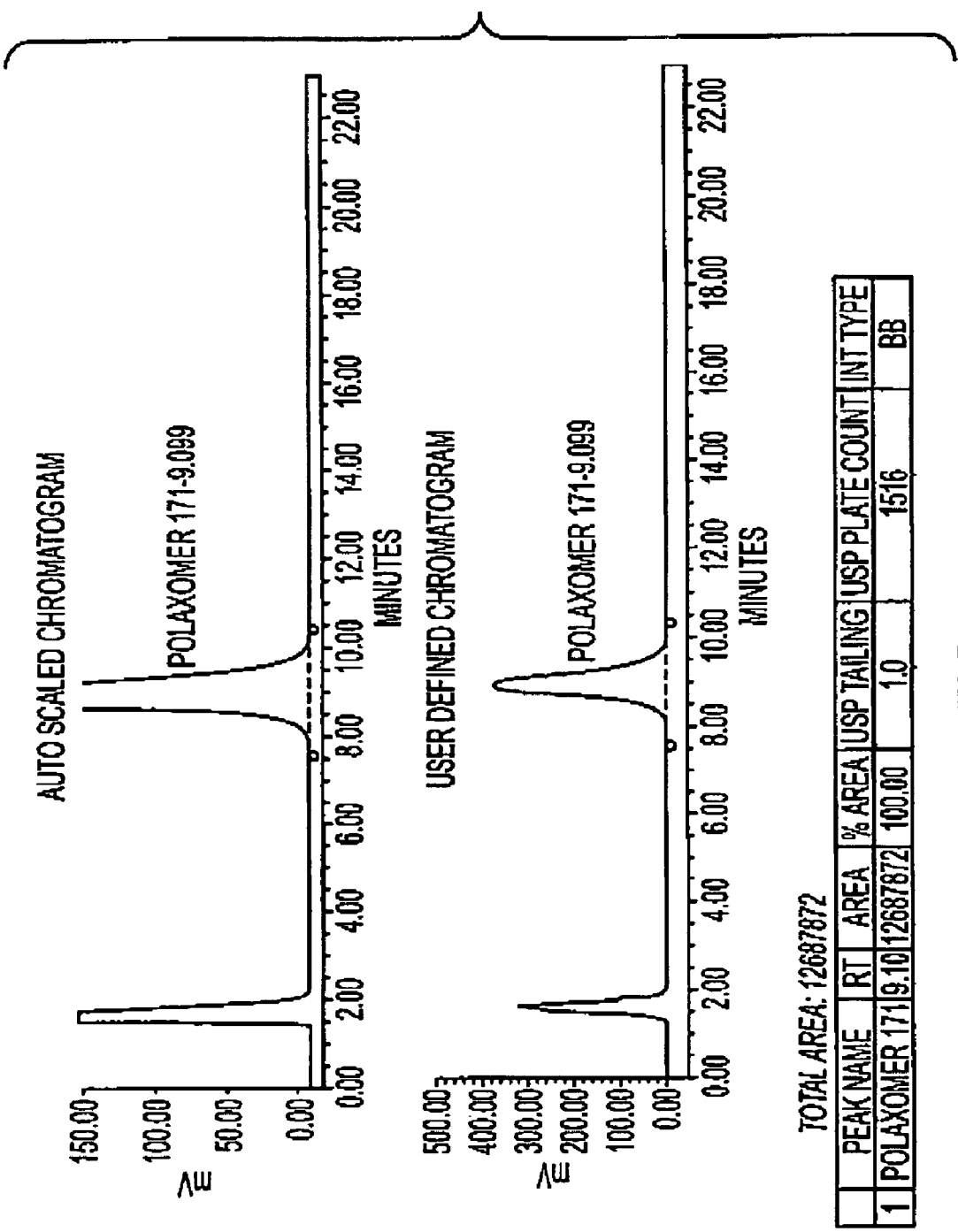
FIG. 5 shows a representative chromatogram of a U400 HRI sample.
Figure 6:
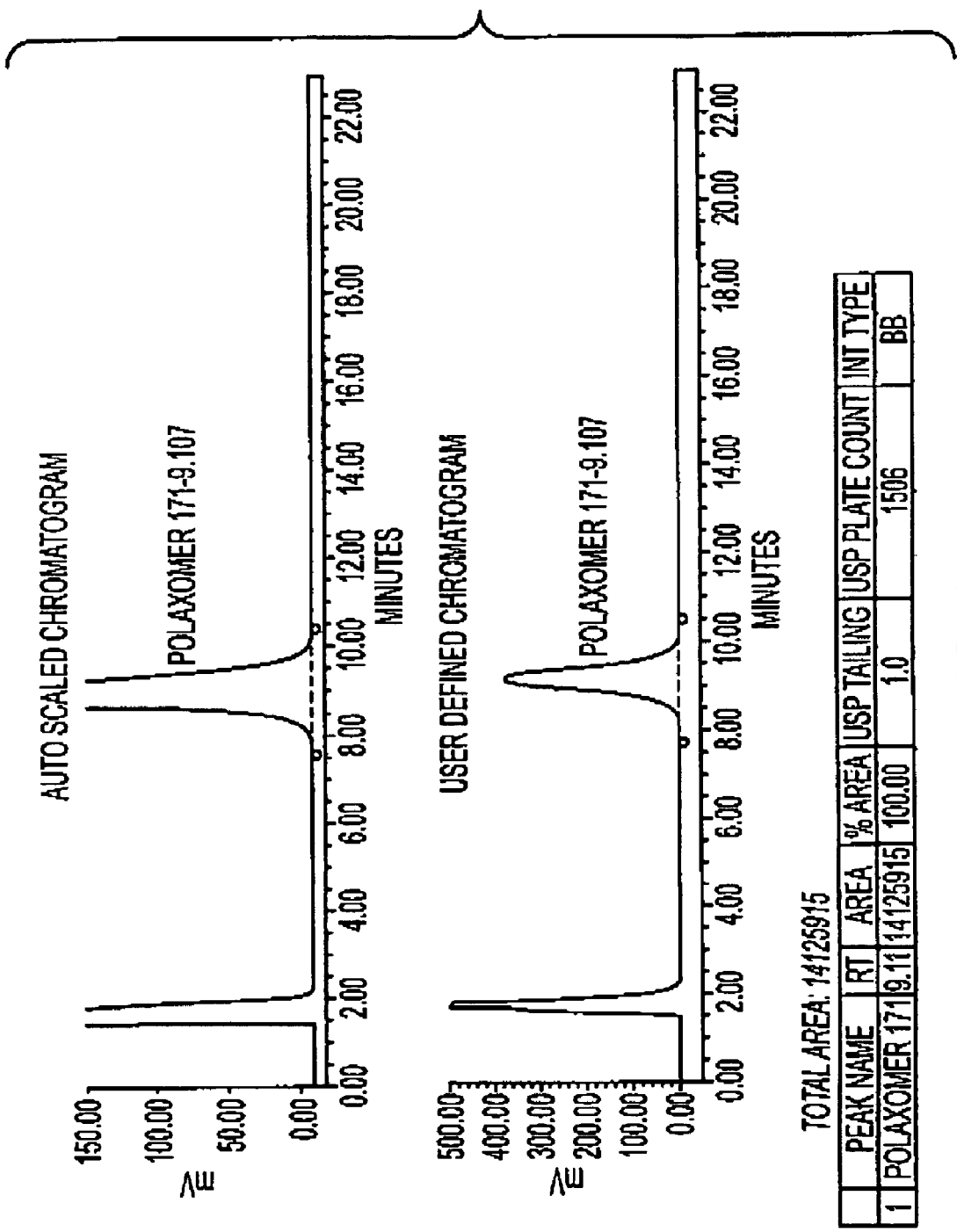
FIG. 6 shows a representative chromatogram of a rinse buffer solution sample.

A. Typical Analyte Sensors, Sensor Elements and Sensor Configurations of the Invention FIG. 2 illustrates a cross-section of a typical sensor structure 100 of the present invention. The sensor is formed from a plurality of layers of various conductive and non-conductive constituents disposed on each other according to a method of the invention to produce a sensor structure. The embodiment shown in FIG. 2 includes a base layer 102 to support the sensor 100. The base layer 102 can be made of a material such as a ceramic or polyimide substrate, which may be self-supporting or further supported by another material as is known in the art. Embodiments of the invention include a conductive layer 104 which is disposed on the base layer 102. Typically the conductive layer 104 includes one or more electrodes. An operating sensor 100 typically includes a plurality of electrodes such as a working electrode, a counter electrode and a reference electrode. Other embodiments may also include an electrode that performs multiple functions, for example one that functions as both as a reference and a counter electrode. Still other embodiments may utilize a separate reference element not formed on the sensor. Typically these electrodes are electrically isolated from each other, while situated in close proximity to one another.

As discussed in detail below, the conductive layer 104 can be applied using many known techniques and materials. The electrical circuit of the sensor is typically defined by etching the disposed conductive layer 104 into a desired pattern of conductive paths. A typical electrical circuit for the sensor 100 includes two or more adjacent conductive paths with regions at a proximal end to form contact pads and regions at a distal end to form sensor electrodes. An electrically insulating cover layer 106 such as a polymer coating is typically disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to for example allow an analyte such as glucose to permeate the layers of the sensor and be sensed by the sensing elements. Apertures 108 can be formed by a number of techniques, including laser ablation, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the sensor configuration shown in FIG. 2, an analyte sensing layer 110 (which is typically a sensor chemistry layer, meaning that materials in this layer undergo a chemical reaction to produce a signal that can be sensed by the conductive layer) is disposed on one or more of the exposed electrodes of the conductive layer 104. Typically, the sensor chemistry layer 110 is an enzyme layer. Most typically, the sensor chemistry layer 110 includes an enzyme capable of producing utilizing oxygen and/or hydrogen peroxide, for example the enzyme glucose oxidase. Typically, the glucose oxidase is in a formulation that contains about 90 KU/mL to about 110 KU/mL glucose oxidase, about 0.12% w/v to about 0.18% w/v potassium sorbate; and about 0.01 M phosphate buffer. Optionally the enzyme in the sensor chemistry layer is combined with a second carrier protein such as human serum albumin, bovine serum albumin or the like. In an illustrative embodiment, an enzyme such as glucose oxidase in the sensor chemistry layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

The analyte sensing layer 110 can be applied over portions of the conductive layer or over the entire region of the conductive layer. Typically the analyte sensing layer 110 is disposed on the working electrode which can be the anode or the cathode. Optionally, the analyte sensing layer 110 is also disposed on a counter and/or reference electrode. Typically, analyte sensing layer 110 is relatively thin as compared to those found in sensors previously described in the art, and is for example, typically less than 1, 0.5, 0.25 or 0.1 microns in thickness. As discussed in detail below, typical methods for generating a thin analyte sensing layer 110 include spin coating processes, dip and dry processes, low shear spraying processes, ink-jet printing processes, silk screen processes and the like. Most typically the thin analyte sensing layer 110 is applied using a spin coating process.

Typically, the analyte sensing layer 110 is coated with one or more additional layers. Optionally, the one or more additional layers includes a protein layer 116 disposed upon the analyte sensing layer 110. Typically, the protein layer 116 includes a protein such as albumin or the like. Typically, the protein layer 116 includes human serum albumin. In some embodiments of the invention, an additional layer includes an analyte modulating layer 112 that is disposed above the analyte sensing layer 110 to regulate analyre contact with the analyte sensing layel 110. For example, the analyte modulating membrane layer 112 can include a glucose limiting membraric, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimnethyl siloxanes, polyuzethanes, polyurea cellulose acetates, NAFION (a sulfonated terrafluorethylene copolymer), polyester sulfonic acids (e.g. Kodak AQ), hydrogels or any other suitable hydrophilic membranes known to those skilled in the art.

In typical embodiments of the invention, an adhesion promoter layer 114 is disposed between the analyte modulating layer 112 and the analyte sensing layer 110 as shown in FIG. 2 in order to facilitate their contact and/or adhesion. In a specific embodiment of the invention, an adhesion promoter layer 114 is disposed between the analyte modulating layer 112 and the protein layer 116 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 includes a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

The analyte sensor apparatus has a number of embodiments. A general embodiment of the invention is an analyte sensor apparatus for implantation within a mammal. While the analyte sensors are typically designed to be implantable within the body of a mammal, the sensor are not limited to any particular environment can instead be used in a wide variety of contexts, for example for the analysis of most liquid samples including biological fluids such as whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

As noted above, the sensor embodiments can be used to sense analytes of interest in one or more physiological environments. In certain embodiments for example, the sensor can be in direct contact with interstitial fluids as typically occurs with subcutaneous sensors. The sensors of the present invention may also be part of a skin surface system where interstitial glucose is extracted through the skin and brought into contact with the sensor (see, e.g. U.S. Pat. Nos. 6,155,992 and 6,706,159 which are incorporated herein by reference). In other embodiments, the sensor can be in contact with blood as typically occurs for example with intravenous sensors. The sensor embodiments of the invention further include those adapted for use in a variety of contexts. In certain embodiments for example, the sensor can be designed for use in mobile contexts, such as those employed by ambulatory users. Alternatively, the sensor can be designed for use in stationary contexts such as those adapted for use in clinical settings. Such sensor embodiments include for example those used to monitor one or more analytes present in one or more physiological environments in a hospitalized patient.

Sensors of the invention can also be incorporated in to a wide variety of medical systems known in the art. Sensors of the invention can be used for example in a closed loop infusion systems designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. Typically, the sensor is a subcutaneous sensor in contact with interstitial fluid to monitor the glucose concentration in the body of the user, and the liquid infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

Certain embodiments of the invention measure peroxide and have the advantageous characteristic of being suited for implantation in a variety of sites in the mammal including regions of subcutaneous implantation and intravenous implantation as well as implantation into a variety of non-vascular regions. A peroxide sensor design that allows implantation into non-vascular regions has advantages over certain sensor apparatus designs that measure oxygen due to the problems with oxygen noise that can occur in oxygen sensors implanted into non-vascular regions. For example in such implanted oxygen sensor apparatus designs, oxygen noise at the reference sensor can compromise the signal to noise ratio which consequently perturbs their ability to obtain stable glucose readings in this environment. The peroxide sensors of the invention therefore overcome the difficulties observed with such oxygen sensors in non-vascular regions.

Certain peroxide sensor embodiments of the invention further include advantageous long term or "permanent" sensors which are suitable for implantation in a mammal for a time period of greater than 30 days. In particular, as is known in the art (see, e.g. ISO 10993, Biological Evaluation of Medical Devices) medical devices such as the sensors can be categorized into three groups based on implant duration: (1) "Limited" (<24 hours), (2) "Prolonged" (24 hours-30 days), and (3) "Permanent" (>30 days). In some embodiments of the invention, the design of the peroxide sensor of the invention allows for a "Permanent" implantation according to this categorization, i.e. >30 days. In related embodiments of the invention, the highly stable design of the peroxide sensor of the invention allows for an implanted sensor to continue to function in this regard for 2, 3, 4, 5, 6 or 12 or more months.

In general, the analyte sensor apparatus structure includes a base layer and a conductive layer disposed upon the base layer that includes one or more electrodes. For example, the conductive layer can include a working electrode, a reference electrode and/or a counter electrode. These electrodes can be spaced in proximity, or alternatively are spaced distally according to the design. The sensor apparatus design is such that certain electrodes (e.g. the working electrode) can be exposed to the solution containing the analyte to be sensed (e.g. via an aperture) in the sensor apparatus. The sensor apparatus design is such that certain electrodes (e.g. the reference electrode) are not exposed to the solution containing the analyte to be sensed in the sensor apparatus.

Typically, the analyte sensor apparatus includes an analyte sensing layer disposed on the conductive layer, typically covering a portion or all of the working electrode. This analyte sensing layer detectably alters the electrical current at the working electrode in the conductive layer in the presence of an analyte to be sensed. This analyte sensing layer typically includes an enzyme or antibody molecule or the like that reacts with the analyte of interest in a manner that changes the concentrations of a molecule that can modulate the current at the working electrode (see e.g. oxygen and/or hydrogen peroxide as shown in the reaction scheme of FIG. 1). Illustrative analyte sensing layers include an enzyme such as glucose oxidase (e.g. for use in glucose sensors). Typically, the analyte sensing layer further includes a carrier protein in a substantially fixed ratio with the analyte sensing compound (e.g. the enzyme) and the analyte sensing compound and the carrier protein are distributed in a substantially uniform manner throughout the analyte sensing layer. Typically the analyte sensing layer is very thin for example less than 1, 0.5, 0.25 or 0.1 microns in thickness. While not being bound by a specific scientific theory, it is believed that sensors having such thin analyte sensing layers have surprisingly enhanced characteristics as compared to the thicker layers that are typically generated by electrodeposition because electrodeposition produces 3-5 micron thick enzyme layers in which only a fraction of the reactive enzyme within the coating layer is able to access the analyte to be sensed. Such thicker glucose oxidase pellets that are produced by electrodeposition protocols are further observed to have a poor mechanical stability (e.g. a tendency to crack) and further take a longer time to prepare for actual use, typically taking weeks of testing before it is ready for implantation. As these problems are not observed with the thin layered enzyme coatings, these thin coatings are embodiments of the invention.

In sensors utilizing glucose oxidase for example, the thick coatings produced by electrodeposition may hinder the ability of hydrogen peroxide generated at the reactive interface of the 3-5 micron thick enzyme layer to contact the sensor surface and thereby generate a signal. In addition, hydrogen peroxide that is unable to reach a sensor surface due to such thick coatings can diffuse away from the sensor into the environment in which the sensor is placed, thereby decreasing the sensitivity and/or biocompatibility of such sensors. Moreover, while not being bound by a specific scientific theory, it is believed that sensors having such thin analyte sensing layers have unexpectedly advantageous properties that result from the fact that processes such as spin coating, or the like, allow for a precise control over the enzyme coating's ratio of glucose oxidase to albumin (which is used as a carrier protein to stabilize the glucose oxidase in the enzyme layer). Specifically, because glucose oxidase and albumin have different isoelectric points, electrodeposition processes may result in a surface coating in which an optimally determined ratio of enzyme to carrier protein is detrimentally altered in the electrodeposition process and further where the glucose oxidase and the carrier protein are not distributed in a substantially uniform manner throughout the disposed enzyme layer. In addition, sensors having such thin analyte sensing layers have unexpectedly faster response times. While not being bound by a specific scientific theory, it is believed that these surprising and advantageous properties result from the fact that thin enzyme layers allow a better access to the working electrode surface and may allow a greater proportion of the molecules that modulate current at the electrode to access the electrode surface. In this context, in certain sensor embodiments of the invention, an alteration in current in response to exposure to the analyte present in the body of the mammal can be detected via an amperometer within 15, 10, 5 or 2 minutes of the analyte contacting the analyte sensor.

Optionally, the analyte sensing layer has a protein layer disposed thereon and which it typically between this analyte sensing layer and the analyte modulating layer. A protein within the protein layer is an albumin selected from the group consisting of bovine serum albumin and human serum albumin. Typically this protein is crosslinked. Without being bound by a specific scientific theory, it is believed that this separate protein layer enhances sensor function provides surprising functional benefits by acting as a sort of capacitor that diminishes sensor noise (e.g. spurious background signals). For example, in the sensors of the invention, some amount of moisture may form under the analyte modulating membrane layer of the sensor, the layer which regulates the amount of analyte that can contact the enzyme of the analyte sensing layer. This moisture may create a compressible layer that shifts within the sensor as a patient using the sensor moves. Such shifting of layers within the sensor may alter the way that an analyte such as glucose moves through the analyte sensing layers in a manner that is independent of actual physiological analyte concentrations, thereby generating noise. In this context, the protein layer may act as a capacitor by protecting an enzyme such as GOx from contacting the moisture layer. This protein layer may confer a number of additional advantages such as promoting the adhesion between the analyte sensing layer and the analyte modulating membrane layer. Alternatively, the presence of this layer may result in a greater diffusion path for molecules such as hydrogen peroxide, thereby localizing it to the electrode sensing element and contributing to an enhanced sensor sensitivity.

Typically, the analyte sensing layer and/or the protein layer disposed on the analyte sensing layer has an adhesion promoting layer disposed thereon. Such adhesion promoting layers promote the adhesion between the analyte sensing layer and a proximal layer, typically an analyte modulating layer. This adhesion promoting layer preferably includes a silane compound such as γ-aminopropyltrimethoxysilane which is selected for its ability to promote optimized adhesion between the various sensor layers and functions to stabilize the sensor. Interestingly sensors having such a silane containing adhesion promoting layers exhibit unexpected properties including an enhanced overall stability. In addition, silane containing adhesion promoting layers provide a number of advantageous characteristics in addition to an ability to enhancing sensor stability and can for example play a beneficial role in interference rejection as well as in controlling the mass transfer of one or more desired analytes.

In certain embodiments of the invention, the adhesion promoting layer further includes one or more compounds that can also be present in an adjacent layer such as the polydimethyl siloxane (PDMS) compounds that serves to limit the diffusion of analytes such as glucose through the analyte modulating layer. The addition of PDMS to the AP layer for example can be advantageous in contexts where it diminishes the possibility of holes or gaps occurring in the AP layer as the sensor is manufactured.

Typically the adhesion promoting layer has an analyte modulating layer disposed thereon which functions to modulate the diffusion of analytes therethrough. In one embodiment, the analyte modulating layer includes compositions (e.g. polymers and the like) which serves to enhance the diffusion of analytes (e.g. oxygen) through the sensor layers and consequently function to enrich analyte concentrations in the analyte sensing layer. Alternatively, the analyte modulating layer includes compositions which serve to limit the diffusion of analytes (e.g. glucose) through the sensor layers and consequently function to limit analyte concentrations in the analyte sensing layer. An illustrative example of this is a hydrophilic glucose limiting membrane (i.e. functions to limit the diffusion of glucose therethrough) including a polymer such as polydimethyl siloxane or the like.

Typically the analyte modulating layer further includes one or more cover layers which are typically electrically insulating protective layers a cover layer disposed on at least a portion of the sensor apparatus (e.g. covering the analyte modulating layer). Acceptable polymer coatings for use as the insulating protective cover layer can include, but are not limited to, non-toxic biocompatible polymers such as silicone compounds, polyimides, biocompatible solder masks, epoxy acrylate copolymers, or the like. An illustrative cover layer includes spun on silicone. Typically the cover layer further includes an aperture that exposes at least a portion of a sensor layer (e.g. analyte modulating layer) to a solution including the analyte to be sensed.

The analyte sensors can be polarized cathodically to detect for example, changes in current at the working cathode that result from the changes in oxygen concentration proximal to the working cathode that occur as glucose interacts with glucose oxidase as shown in FIG. 1. Alternatively, the analyte sensors can be polarized anodically to detect for example, changes in current at the working anode that result from the changes in hydrogen peroxide concentration proximal to the working anode that occur as glucose interacts with glucose oxidase as shown in FIG. 1. In typical embodiments of the invention, the current at the working electrode(s) are compared to the current at a reference electrode(s) (a control), with the differences between these measurements providing a value that can then be correlated to the concentration of the analyte being measured. Analyte sensor designs that obtain a current value by obtaining a measurement from a comparison of the currents at these dual electrodes are commonly termed, for example, dual oxygen sensors.

B. Illustrative Methods and Materials for Making Analyte Sensor Apparatus of the Invention A number of articles, U.S. patents and patent application describe the state of the art with the common methods and materials and further describe various elements (and methods for their manufacture) that can be used in the sensor designs. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al.,: "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al.,: "In Vivo Measurement of Subcutaneous Glucose Concentrations with an Enzymatic Glucose Sensor and a Wick Method," Klin. Wochenschr. 67:491-495 (1989); and Pickup, et al.,: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

A typical embodiment of the invention is a method of making a sensor apparatus for implantation within a mammal including the steps of: providing a base layer; forming a conductive layer on the base layer, where the conductive layer includes an electrode (and typically a working electrode, a reference electrode and a counter electrode); forming an analyte sensing layer on the conductive layer, where the analyte sensing layer is formed using a composition including glucose oxidase, where the glucose oxidase is present in a concentration of about 90 KU/mL to about 110 KU/mL; potassium sorbate, where the potassium sorbate is present in a concentration of about 0.12% w/v to about 0.18% w/v; and a potassium phosphate buffer; where the potassium phosphate buffer is present in a concentration of about 0.01 M; optionally forming a protein layer on the analyte sensing layer; forming an adhesion promoting layer on the analyte sensing layer or the optional protein layer; forming an analyte modulating layer disposed on the adhesion promoting layer, where the analyte modulating layer includes a composition that modulates the diffusion of the analyte therethrough; and forming a cover layer disposed on at least a portion of the analyte modulating layer, where the cover layer further includes an aperture over at least a portion of the analyte modulating layer. In certain embodiments of these methods, the analyte sensor apparatus is formed in a planar geometric configuration.

The various layers of the sensor can be manufactured to exhibit a variety of different characteristics which can be manipulated according to the design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

Typically a method of making the sensor includes the step of forming a protein layer on the analyte sensing layer, where a protein within the protein layer is an albumin selected from the group consisting of bovine serum albumin and human serum albumin. Typically a method of making the sensor includes the step of forming an analyte sensing layer from a formulation including glucose oxidase, where the glucose oxidase is present in a concentration of about 90 KU/mL to about 110 KU/mL; potassium sorbate, where the potassium sorbate is present in a concentration of about 0.12% w/v to about 0.18% w/v; and a potassium phosphate buffer; where the potassium phosphate buffer is present in a concentration of about 0.01 M. In such methods, the analyte sensing layer typically includes a carrier protein composition in a substantially fixed ratio with the enzyme and the enzyme and the carrier protein are distributed in a substantially uniform manner throughout the analyte sensing layer.

The disclosure includes sensors and sensor designs that can be generated using combinations of various well known techniques. The disclosure further provides methods for applying very thin enzyme coatings to these types of sensors as well as sensors produced by such processes. In this context, some embodiments of the invention include methods for making such sensors on a substrate according to art accepted processes. In certain embodiments, the substrate includes a rigid and flat structure suitable for use in photolithographic mask and etch processes. In this regard, the substrate typically defines an upper surface having a high degree of uniform flatness. A polished glass plate may be used to define the smooth upper surface. Alternative substrate materials include, for example, stainless steel, aluminum, and plastic materials such as delrin, etc. In other embodiments, the substrate is non-rigid and can be another layer of film or insulation that is used as a substrate, for example plastics such as polyimides and the like.

An initial step in the methods of the invention typically includes the formation of a base layer of the sensor. The base layer can be disposed on the substrate by any desired means, for example by controlled spin coating. In addition, an adhesive may be used if there is not sufficient adhesion between the substrate layer and the base layer. A base layer of insulative material is formed on the substrate, typically by applying the base layer material onto the substrate in liquid form and thereafter spinning the substrate to yield the base layer of thin, substantially uniform thickness. These steps are repeated to build up the base layer of sufficient thickness, followed by a sequence of photolithographic and/or chemical mask and etch steps to form the conductors discussed below. In one form, the base layer includes a thin film sheet of insulative material, such as ceramic or polyimide substrate. The base layer can include an alumina substrate, a polyimide substrate, a glass sheet, controlled pore glass, or a planarized plastic liquid crystal polymer. The base layer may be derived from any material containing one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof. Additionally, the substrate may be coated onto a solid support by a variety of methods well-known in the art including chemical vapor deposition, physical vapor deposition, or spin-coating with materials such as spin glasses, chalcogenides, graphite, silicon dioxide, organic synthetic polymers, and the like.

The methods of the invention further include the generation of a conductive layer having one or more sensing elements. Typically these sensing elements are electrodes that are formed by one of the variety of methods known in the art such as photoresist, etching and rinsing to define the geometry of the active electrodes. The electrodes can then be made electrochemically active, for example by electrodeposition of Pt black for the working and counter electrode, and silver followed by silver chloride on the reference electrode. A sensor layer such as a sensor chemistry enzyme layer can then be disposed on the sensing layer by electrochemical deposition or a method other than electrochemical deposition such a spin coating, followed by vapor crosslinking, for example with a dialdehyde (glutaraldehyde) or a carbodiimide.

Electrodes of the invention can be formed from a wide variety of materials known in the art. For example, the electrode may be made of a noble late transition metals. Metals such as gold, platinum, silver, rhodium, iridium, ruthenium, palladium, or osmium can be suitable in various embodiments of the invention. Other compositions such as carbon or mercury can also be useful in certain sensor embodiments. Of these metals, silver, gold, or platinum is typically used as a reference electrode metal. A silver electrode which is subsequently chloridized typically used as the reference electrode. These metals can be deposited by any means known in the art, including the plasma deposition method cited, supra, or by an electroless method which may involve the deposition of a metal onto a previously metallized region when the substrate is dipped into a solution containing a metal salt and a reducing agent. The electroless method proceeds as the reducing agent donates electrons to the conductive (metallized) surface with the concomitant reduction of the metal salt at the conductive surface. The result is a layer of adsorbed metal. (For additional discussions on electroless methods, see: Wise, E. M. Palladium: Recovery, Properties, and Uses, Academic Press, New York, N.Y. (1988); Wong, K. et al. Plating and Surface Finishing 1988, 75, 70-76; Matsuoka, M. et al. Ibid. 1988, 75, 102-106; and Pearlstein, F. "Electroless Plating," Modern Electroplating, Lowenheim, F. A., Ed., Wiley, New York, N.Y. (1974), Chapter 31.). Such a metal deposition process must yield a structure with good metal to metal adhesion and minimal surface contamination, however, to provide a catalytic metal electrode surface with a high density of active sites. Such a high density of active sites is a property necessary for the efficient redox conversion of an electroactive species such as hydrogen peroxide.

In an exemplary embodiment of the invention, the base layer is initially coated with a thin film conductive layer by electrode deposition, surface sputtering, or other suitable process step. In one form, this conductive layer may be provided as a plurality of thin film conductive layers, such as an initial chrome-based layer suitable for chemical adhesion to a polyimide base layer followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base layer. In an illustrative sensor construction designed for use as a subcutaneous glucose sensor, each sensor trace can include three parallel sensor elements corresponding with three separate electrodes such as a working electrode, a counter electrode and a reference electrode.

Portions of the conductive sensor layers are typically covered by a insulative cover layer, typically of a material such as a silicon polymer and/or a polyimide. The insulative cover layer can be applied in any desired manner. In an exemplary procedure, the insulative cover layer is applied in a liquid layer over the sensor traces, after which the substrate is spun to distribute the liquid material as a thin film overlying the sensor traces and extending beyond the marginal edges of the sensor traces in sealed contact with the base layer. This liquid material can then be subjected to one or more suitable radiation and/or chemical and/or heat curing steps as are known in the art. In alternative embodiments, the liquid material can be applied using spray techniques or any other desired means of application. Various insulative layer materials may be used such as photoimagable epoxyacrylate, with a illustrative material including a photoimagable polyimide available from OCG, Inc. of West Paterson, N.J., under the product number 7020.

As noted above, appropriate electrode chemistries defining the distal end electrodes can be applied to the sensor tips, optionally subsequent to exposure of the sensor tips through the openings. In an illustrative sensor embodiment having three electrodes for use as a glucose sensor, an enzyme (typically glucose oxidase) is provided within one of the openings, thus coating one of the sensor tips to define a working electrode. One or both of the other electrodes can be provided with the same coating as the working electrode. Alternatively, the other two electrodes can be provided with other suitable chemistries, such as other enzymes, left uncoated, or provided with chemistries to define a reference electrode and a counter electrode for the electrochemical sensor.

Aspects of the present invention can include processes for making sensors having extremely thin coatings for electrode chemistries (e.g., glucose oxidase coatings of less than 2 microns in thickness) with enhanced material properties. Methods for producing the extremely thin enzyme coatings of the invention include spin coating processes, dip and dry processes, low shear spraying processes, ink-jet printing processes, silk screen processes and the like. As artisans can readily determine the thickness of an enzyme coat applied by process of the art, they can readily identify those methods capable of generating the extremely thin coatings of the invention. Typically, such coatings are vapor crosslinked subsequent to their application. Surprisingly, sensors produced by these processes have material properties that exceed those of sensors having coatings produced by electrodeposition including enhanced longevity, linearity, regularity as well as improved signal to noise ratios. In addition, embodiments of the invention that utilize glucose oxidase coatings formed by such processes are designed to recycle hydrogen peroxide and improve the biocompatibility profiles of such sensors.

While not being bound by a specific scientific theory, it is believed that the surprising properties of sensors produced by such processes have enhanced characteristics as compared to those generated by electrodeposition because electrodeposition produces 3-5 micron thick enzyme layers in which only a fraction of the reactive enzyme is able to access the analyte to be sensed. Moreover, in sensors utilizing glucose oxidase, the thick coatings produced by electrodeposition may hinder the ability of hydrogen peroxide generated at the reactive interface to reach the sensor surface and thereby generate a signal. Moreover, hydrogen peroxide that is unable to reach a sensor surface due to such thick coatings typically diffuses away from the sensor into the environment in which the sensor is placed, thereby decreasing the biocompatibility of such sensors. In addition, as glucose oxidase and albumin have different isoelectric points, electrodeposition processes can result in a surface coating in which an optimally determined ratio of enzyme to carrier protein is detrimentally altered and further where the glucose oxidase and the carrier protein are not distributed in a substantially uniform manner throughout the disposed enzyme layer. The thin coating processes utilized to produce sensors that avoid these problems associated with electrodeposition.

Sensors generated by processes such as spin coating processes also avoid other problems associated with electrodeposition, such as those pertaining to the material stresses placed on the sensor during the electrodeposition process. In particular, the process of electrodeposition is observed to produce mechanical stresses on the sensor, for example mechanical stresses that result from tensile and/or compression forces. In certain contexts, such mechanical stresses may result in sensors having coatings with some tendency to crack or delaminate. This is not observed in coatings disposed on sensor via spin coating or other low-stress processes. Consequently, yet another embodiment of the invention is a method of avoiding the electrodeposition influenced cracking and or delamination of a coating on a sensor including applying the coating via a spin coating process.

Subsequent to treatment of the sensor elements, one or more additional functional coating or cover layers can then be applied by any one of a wide variety of methods known in the art, such as spraying, dipping, etc. Some embodiments of the present invention include an analyte modulating layer deposited over the enzyme-containing layer. In addition to its use in modulating the amount of analyte(s) that contacts the active sensor surface, by utilizing an analyte limiting membrane layer, the problem of sensor fouling by extraneous materials is also obviated. As is known in the art, the thickness of the analyte modulating membrane layer can influence the amount of analyte that reaches the active enzyme. Consequently, its application is typically carried out under defined processing conditions, and its dimensional thickness is closely controlled. As in the microfabrication of the underlying layers can be a factor which affects close dimensional control over the analyte modulating membrane layer is the composition of the analyte limiting membrane layer material itself. In this regard, it has been discovered that several types of copolymers, for example, a copolymer of a siloxane and a nonsiloxane moiety, are particularly useful. These materials can be microdispensed or spin-coated to a controlled thickness. Their final architecture may also be designed by patterning and photolithographic techniques in conformity with the other discrete structures. Examples of these nonsiloxane-siloxane copolymers include, but are not limited to, dimethylsiloxane-alkene oxide, tetramethyldisiloxane-divinylbenzene, tetramethyld-isiloxane-ethylene, dimethylsiloxane-silphenylene, dimethylsiloxane-silphenylene oxide, dimethylsiloxane-a-methylstyrene, dimethylsiloxane-bisphenol A carbonate copolymers, or suitable combinations thereof. The percent by weight of the nonsiloxane component of the copolymer can be preselected to any useful value but typically this proportion lies in the range of about 40-80 wt %. These materials may be purchased from Petrarch Systems, Bristol, Pa. (USA) and are described in this company's products catalog. Other materials which may serve as analyte limiting membrane layers include, but are not limited to, polyurethanes, cellulose acetate, cellulose nitrate, silicone rubber, or combinations of these materials including the siloxane non-siloxane copolymer, where compatible.

In some embodiments of the invention, the sensor is made by methods which apply an analyte modulating layer that includes a hydrophilic membrane coating which can regulate the amount of analyte that can contact the enzyme of the sensor layer. For example, the cover layer that is added to the glucose sensors of the invention can include a glucose limiting membrane, which regulates the amount of glucose that contacts glucose oicidase enzyme layer on an electrode. Such glucose limiting membranes can be made from a wick variety of materials known to be suitable for such purposes, e.g., silicones such as polydimethyl sioxane and the like, polyuxethanes, cellulose acetates, NAFION (a sulfonated tetrafluorethylene copolymer), polyester sulfonic acids (e.g. Kodak AQ). hydrogels or any other membrane known to those skilled in the art that is suitable for such purposes. In certain embodiments of the invention pertaining to sensors having hydrogen peroxide recycling capabilities, the membrane layer that is disposed on the glucose oxidase enzyme layer functions to inhibit the release of hydrogen preoxide into the environment in which the sensor is placed and to facilitate the contact between the hydrogen peroxide molecules and the electrode sensing elements.

In some embodiments of the methods of invention, an adhesion promoter layer is disposed between a cover layer (e.g. an analyte modulating membrane layer) and a sensor chemistry layer in order to facilitate their contact and is selected for its ability to increase the stability of the sensor apparatus. Compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art. Typically, the adhesion promoter layer includes a silane compound such as γ-aminopropyltrimethoxysilane. In certain embodiments of the invention, the adhesion promoting layer and/or the analyte modulating layer includes an agent selected for its ability to crosslink a siloxane moiety present in a proximal. In other embodiments of the invention, the adhesion promoting layer and/or the analyte modulating layer includes an agent selected for its ability to crosslink an amine or carboxyl moiety of a protein present in a proximal layer. In an optional embodiment, the AP layer further includes Polydimethyl Siloxane (PDMS), a polymer typically present in analyte modulating layers such as a glucose limiting membrane. In illustrative embodiments the formulation includes 0.5-20% PDMS, typically 5-15% PDMS, and most typically 10% PDMS. The addition of PDMS to the AP layer can be advantageous in contexts where it diminishes the possibility of holes or gaps occurring in the AP layer as the sensor is manufactured.

As noted above, a coupling reagent commonly used for promoting adhesion between sensor layers is γ-aminopropyltrimethoxysilane. The silane compound is usually mixed with a suitable solvent to form a liquid mixture. The liquid mixture can then be applied or established on the wafer or planar sensing device by any number of ways including, but not limited to, spin-coating, dip-coating, spray-coating, and microdispensing. The microdispensing process can be carried out as an automated process in which microspots of material are dispensed at multiple preselected areas of the device. In addition, photolithographic techniques such as "lift-off" or using a photoresist cap may be used to localize and define the geometry of the resulting permselective film (i.e. a film having a selective permeability). Solvents suitable for use in forming the silane mixtures include aqueous as well as water-miscible organic solvents, and mixtures thereof. Alcoholic water-miscible organic solvents and aqueous mixtures thereof are particularly useful. These solvent mixtures may further include nonionic surfactants, such as polyethylene glycols (PEG) having a for example a molecular weight in the range of about 200 to about 6,000. The addition of these surfactants to the liquid mixtures, at a concentration of about 0.005 to about 0.2 g/dL of the mixture, aids in planarizing the resulting thin films. Also, plasma treatment of the wafer surface prior to the application of the silane reagent can provide a modified surface which promotes a more planar established layer. Water-immiscible organic solvents may also be used in preparing solutions of the silane compound. Examples of these organic solvents include, but are not limited to, diphenylether, benzene, toluene, methylene chloride, dichloroethane, trichloroethane, tetrachloroethane, chlorobenzene, dichlorobenzene, or mixtures thereof. When protic solvents or mixtures thereof are used, the water eventually causes hydrolysis of the alkoxy groups to yield organosilicon hydroxides (especially when n=1) which condense to form poly(organosiloxanes). These hydrolyzed silane reagents are also able to condense with polar groups, such as hydroxyls, which may be present on the substrate surface. When aprotic solvents are used, atmospheric moisture may be sufficient to hydrolyze the alkoxy groups present initially on the silane reagent. The R' group of the silane compound (where n=1 or 2) is chosen to be functionally compatible with the additional layers which are subsequently applied. The R' group usually contains a terminal amine group useful for the covalent attachment of an enzyme to the substrate surface (a compound, such as glutaraldehyde, for example, may be used as a linking agent as described by Murakami, T. et al., Analytical Letters 1986, 19, 1973-86).

Like certain other coating layers of the sensor, the adhesion promoter layer can be subjected to one or more suitable radiation and/or chemical and/or heat curing steps as are known in the art. In alternative embodiments, the enzyme layer can be sufficiently crosslinked or otherwise prepared to allow the membrane cover layer to be disposed in direct contact with the sensor chemistry layer in the absence of an adhesion promoter layer.

One embodiment of the invention is a method of making a sensor by providing a base layer, forming a sensor layer on the base layer, spin coating an enzyme layer on the sensor layer and then forming an analyte contacting layer (e.g. an analyte modulating layer such as a glucose limiting membrane) on the sensor, where the analyte contacting layer regulates the amount of analyte that can contact the enzyme layer. In some methods, the enzyme layer is vapor crosslinked on the sensor layer. In a typical embodiment of the invention, the sensor layer is formed to include at least one working electrode and at least one counter electrode. In some embodiments, the enzyme layer is formed on at least a portion of the working electrode and at least a portion of the counter electrode. Typically, the enzyme layer is formed using a formulation including glucose oxidase, where the glucose oxidase is present in a concentration of about 90 KU/mL to about 110 KU/mL; potassium sorbate, where the potassium sorbate is present in a concentration of about 0.12% w/v to about 0.18% w/v; and a potassium phosphate buffer; where the potassium phosphate buffer is present in a concentration of about 0.01 M. In a specific method, the enzyme layer includes glucose oxidase that is stabilized by coating it on the sensor layer in combination with a carrier protein in a fixed ratio. Typically the carrier protein is albumin. Typically such methods include the step of forming an adhesion promoter layer disposed between the glucose oxidase layer and the analyte contacting layer. Optionally, the adhesion promoter layer is subjected to a curing process prior to the formation of the analyte contacting layer.

A related embodiment of the invention is a method of making a glucose sensor by providing a base layer, forming a sensor layer on the base layer that includes at least one working electrode and at least one counter electrode, forming a glucose oxidase layer on the sensor layer by a spin coating process (a layer which is typically stabilized by combining the glucose oxidase with albumin in a fixed ratio), where the glucose oxidase layer coats at least a portion of the working electrode and at least a portion of the counter electrode, and then forming a glucose limiting layer on the glucose sensor so as to regulate the amount of glucose that can contact the glucose oxidase layer. Typically, the glucose oxidase is in a formulation that contains about 90 KU/mL to about 110 KU/mL glucose oxidase, about 0.12% w/v to about 0.18% w/v potassium sorbate; and about 0.01 M phosphate buffer. In such processes, the glucose oxidase layer that is formed on the sensor layer is typically less than 2, 1, 0.5, 0.25 or 0.1 microns in thickness. Typically, the glucose oxidase coating is vapor crosslinked on the sensor layer. Optionally, the glucose oxidase coating covers the entire sensor layer. In some embodiments of the invention, an adhesion promoter layer disposed between the glucose oxidase layer and the analyte contacting layer. In certain embodiments of the invention, the analyte sensor further includes one or more cover layers which are typically electrically insulating protective layers (see, e.g. element 106 in FIG. 2). Typically, such cover layers are disposed on at least a portion of the analyte modulating layer.

C. Methods for Using Analyte Sensor Apparatus of the Invention

Embodiments of the invention include methods of sensing an analyte within the body of a mammal, the method including implanting an analyte sensor embodiment in to the mammal and then sensing an alteration in current at the working electrode and correlating the alteration in current with the presence of the analyte, so that the analyte is sensed. In one such method, the analyte sensor apparatus senses glucose in the mammal. Certain analyte sensors made from the materials and/or having the structure discussed above have a number of highly desirable characteristics which allow for a variety of methods for sensing analytes in a mammal. For example in such methods, the analyte sensor apparatus implanted in the mammal functions to sense an analyte within the body of a mammal for more than 1, 2, 3, 4, 5, or 6 months. Typically, the analyte sensor apparatus so implanted in the mammal senses an alteration in current in response to an analyte within 15, 10, 5 or 2 minutes of the analyte contacting the sensor. In such methods, the sensors can be implanted into a variety of locations within the body of the mammal, for example in both vascular and non-vascular spaces.

III. Kits of the Invention

Embodiments of the invention include a kit and/or sensor set, useful for the sensing an analyte as is described above, is provided. The kit and/or sensor set typically includes a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. In some embodiments, the container holds a glucose sensor coated with a layer of glucose oxidase. Typically, the glucose oxidase layer is prepared from a formulation that contains about 90 KU/mL to about 110 KU/mL glucose oxidase, about 0.12% w/v to about 0.18% w/v potassium sorbate; and about 0.01 M phosphate buffer. The kit and/or sensor set may further include other materials desirable from a commercial and user standpoint, including elements or devices designed to facilitate the introduction of the sensor into the analyte environment, other buffers, diluents, filters, needles, syringes, and package inserts with instructions for use.

The present invention is further detailed in the following Examples, which is offered by way of illustration and are not intended to limit the invention in any manner. All patent and literature references cited in the present specification are hereby incorporated by reference in their entirety.

EXAMPLES

Example 1

Determination of Poloxamer 171 Content in U400 Human Recombinant Insulin (HRI) and Rinse Buffer Solution

This procedure describes the determination of Poloxamer 171 (Genapol) content in U400 human recombinant insulin (HRI) drug product and rinse buffer solution by High Performance Liquid Chromatography with evaporative light scattering detector. In this procedure, Poloxamer 171 is extracted from the sample into ethyl acetate, and then the extract is concentrated. The concentrated extract is then dissolved in methanol, analyzed using an HPLC with evaporative light scattering detection.

This procedure applies to the determination of Poloxamer 171 (Genapol) in human recombinant insulin drug product and rinse buffer solution.

Equipment and Materials:

A high performance liquid chromatograph equipped with an evaporative light scattering detector, a thermostated autosampler, injector, and an appropriate data collection device.
Column: Waters XTerra® MS $C_8$ (4.6×150 mm) 5 µm or a validated equivalent.
Balance(s)
pH meter
Graduated cylinders (Class A)
Volumetric flasks (Class A)
Volumetric pipettes (Class A)
Micropipette
Pipette tips
150 mL round bottomed flasks (24/40)
125 mL separatory funnels, FEP
100 mL beaker
Shaker
Rotary Evaporator
Centrifuge: Beckman Coulter™, Allegra™ 25R with acceleration of 4600 g or equivalent
Centrifuge Tube, 50 mL, polypropylene
Vortex mixer
Nitrogen gas tank Chemicals:
Methanol, high purity solvent
Ethyl acetate, A.C.S reagent
Process water or equivalent
Hydrochloric acid, 6 N, reagent grade minimum
Zinc chloride, reagent grade minimum
Poloxamer 171

Procedure:

Reagent Preparation

Preparation of 0.1 mM Hydrochloric Acid Solution (100 ml)
Pipette 5 ml of 6N hydrochloric acid into a 4000 ml graduated cylinder containing about 2500 ml of process water. Dilute to 3000 ml volume with process water and label as stock solution A. Pipette 1 ml of the stock solution A into a 100 ml graduated cylinder and dilute to volume with process water.

Preparation of Zinc Chloride Solution (50 mL)
Dissolve 2.5 g of zinc chloride in about 5 mL of 0.1 mM hydrochloric acid. Adjust the volume of the solution to 50 mL with process water.

Standard Solution Preparation

Stock Standard Solution Preparation (1250 µg/mL)
Weigh approximately 125 mg of Poloxamer 171 reference standard on an analytical balance. Carefully transfer Poloxamer 171 into a 100 mL volumetric flask containing about 80 mL methanol. Mix well until the Poloxamer 171 dissolves. Make up the volume up to 100 mL with methanol and mix.

Standard Solution 1 (62.5 µg/mL)
Pipette 5.0 mL of stock standard solution into a 100.0 mL volumetric flask and dilute with methanol to the final volume of 100.0 mL.

Standard Solution 2 (100 µg/mL)
Pipette 2.0 mL of stock standard solution into a 25.0 mL volumetric flask and dilute with methanol to the final volume of 25.0 mL.

Standard Solution 3 (125 µg/mL)
Pipette 10.0 mL of stock standard solution into a 100.0 mL volumetric flask and dilute with methanol to the final volume of 100.0 mL.

Standard Solution 4 (150 µg/mL)
Pipette 3.0 mL of stock standard solution into a 25.0 mL volumetric flask and dilute with methanol to the final volume of 25.0 mL.

Standard Solution 5 (187.5 µg/mL)
Pipette 15.0 mL of stock standard solution into a 100.0 mL volumetric flask and dilute with methanol to the final volume of 100.0 mL.
Note: In this method, standards are not extracted.

Analysis Procedure (Sample Preparation and Analysis)

Precipitation of Insulin from U400 HRI (Sample)
Pipette 25.0 mL of each sample into 50 mL centrifuge tube using 25.0 mL volumetric pipette. Add 1.0 mL of zinc chloride solution. Cap each tube then stir the solution using vortex until the solution is mixed well. Allow the mixture to stand at room temperature for at least 30 minutes. Centrifuge the solution for 30 minutes at 4600 g.

Transfer the upper clear solution to a 125 mL separatory funnel (make sure the stop cock of the funnel is in the lock position).

Wash the precipitate with 5 mL of cold process water (5° C.±3° C.) and centrifuge the solution for 30 minutes at 4600 g.

Combine the upper clear solution from wash into the 125 mL separatory funnel.

Preparation of Rinse Buffer Sample Solution
For analysis of Poloxamer 171 in rinse buffer solution, pipette 25.0 mL of the sample into a 125 mL separatory funnel. Rinse buffer solution can be directly extracted and does not need any precipitation steps.

Extraction of Sample Solution
Add 20 mL of ethyl acetate in the separatory funnel. Cap the funnel very well.

Place the separatory funnels on the shaker and shake at a speed of 10 (30 revolutions/min) for 10 minutes.

Take the separatory funnel out of the shaker, point the stem up slowly then open the stopcock to release excess pressure. After the pressure has been released, close the stopcock and place the separatory funnel on a stand. Allow the two layers in the funnel to separate (equilibrate for 5 minutes).

Note: Vent more frequently to prevent pressure buildup, which can cause the stopcock and perhaps hazardous chemicals to blow out.

Loosen the funnel cap and place a 100 mL clean beaker under the funnel. Carefully open the stopcock to let the lower layer (aqueous) drain into the beaker.

Drain out the top organic layer into a clean 150 mL round bottomed flask.

Pour the aqueous layer from the beaker having the lower layer (aqueous) in to the funnel, making sure the funnel stopcock is in the closed position.

Add a second aliquot of 20 mL of ethyl acetate into the funnel, and cap it. Then, repeating the steps above:

Place the separatory funnels on the shaker and shake at a speed of 10 (30 revolutions/min) for 10 minutes.

Take the separatory funnel out of the shaker, point the stem up slowly then open the stopcock to release excess pressure. After the pressure has been released, close the stopcock and place the separatory funnel on a stand. Allow the two layers in the funnel to separate (equilibrate for 5 minutes).

Note: Vent more frequently to prevent pressure buildup, which can cause the stopcock and perhaps hazardous chemicals to blow out.

Loosen the funnel cap and place a 100 mL clean beaker under the funnel. Carefully open the stopcock to let the lower layer (aqueous) drain into the beaker.

Drain out the top organic layer into a clean 150 mL round bottomed flask.

Pour the aqueous layer from the beaker having the lower layer (aqueous) in to the funnel, making sure the funnel stopcock is in the closed position.

Add a third aliquot of 20 mL of ethyl acetate into the funnel, and cap it. Then, repeat the steps above once again with this third aliquot.

Combine the three organic extracts in the same 150 mL round bottomed flask.

Evaporate the ethyl acetate from the extract using a rotary evaporator, where the evaporation is controlled by placing the round bottom flask in a 35° C.±5° C. bath. The extraction solvent (ethyl acetate) should be evaporated completely.

Reconstitute the sample by adding 2 mL methanol (using a 2 mL volumetric pipette) to the 150 mL round flask. Carefully rotate the flask several times to ensure the Poloxamer 171 in the flask is all dissolved into methanol.

Immediately transfer the sample into a 2 mL HPLC vial and cap it very well to prevent the evaporation of methanol.

Sample will be prepared in duplicate and injected into the HPLC.

Instrument Conditions

Detector Conditions
Detection: ELSD Parameters:
Tube Temp: 85±2° C.
Nitrogen gas flow rate: 2.2 l/min
Range: 4
Impactor: Off Chromatographic Conditions
Mobile phase A: 100% Methanol
Mobile phase B: 100% Process water
Sample injection volume: 100 µL
Run Time: 23 minutes Flow rate: 1.0 mL/min
Column temperature: 40±2° C.
Sample temperature: 5° C. (4° C.-7° C.)
Mobile Phase Gradient:

| Time (min) | Flow (mL/min) | % mobile phase A | % mobile phase B |
|---|---|---|---|
|  |  | 80 | 20 |
| 5.0 | 1.0 | 80 | 20 |
| 6.0 | 1.0 | 95 | 5 |
| 12.0 | 1.0 | 95 | 5 |
| 13.0 | 1.0 | 80 | 20 |
| 23.0 | 1.0 | 80 | 20 |

Note:
Adjust the A:B composition as necessary to adjust the Poloxamer 171 peak within the retention time window.

Chromatography

Set up the chromatographic system as discussed above. Methanol is used as blank and injected at the beginning of the sample set. Two injections of blank may be needed to make the clear background.

Inject the standard solution 3 six times. The retention time of Poloxamer 171 peak is between 7 and 12 minutes. If the peak does not fall within this retention window, adjust the eluent composition by adjusting the A:B composition. Increase in mobile phase A will reduce the Poloxamer 171 retention time; Increase in mobile phase B will increase the Poloxamer 171 retention time.

Integrate the peaks (valley to valley—Waters Empower Software) using the data acquisition system. Record the peak area counts of Poloxamer 171 peak from the chromatograms.

System Suitability

System suitability must be determined at the time of sample analysis.

Autoinjector Precision

Determine the peak area of the Poloxamer 171 peak. The % RSD of the area from the six injections must be $\leq 5\%$. If the RSD is greater than 5%, reject the first set of value and inject six more replicates, integrate the peaks and calculate the RSD of the area counts of Poloxamer 171.

Tailing (USP)

Determine the USP tailing for Poloxamer 171 peak from the first injection of the standard solution 3.

The tailing must be $\leq 2.0$. If the tailing is greater than 2.0, system troubleshooting may be necessary.

Sample Analysis Procedure

Separately inject each preparation of standard solution (1, 2, 3, 4 and 5) (in duplicate) and sample solutions (in single). A standard check (standard solution 3) must be injected at the end of the run and at least every 10 sample injections during the run.

Measure and record the area of the Poloxamer 171 peak in the chromatograms of each solution.

Data Analysis

Calculate the average of the area counts for each standard solution from the duplicate injections made.

Determine the logarithm (base 10) of average area count for standard and area count for sample. Plot a least square fit graph of the $\log_{10}$ (Average Standard Area) versus the $\log_{10}$ (concentration) for the standard injections.

Determine the correlation coefficient, slope and intercept of the standard curve.

Determine the concentration of Poloxamer 171 content in U400 HRI using the following formula Poloxamer 171 Content (μg/mL) =

$$\text{Anti } \log_{10}\left[\frac{\{\log_{10}(SampleArea) - \text{Intercept}\}}{\text{Slope}}\right] \times \text{Dilution Factor}/0.94$$

Where Dilution Factor=2/25.

The average of the two preparations will be reported. Report results to two numbers after the decimal place (0.01).

Note: For U400 HRI sample determination, 0.94 revovry factor is added into the calculation based on the validation results.

Determine the concentration of Poloxamer 171 content in Rinse Buffer Solution following formula Poloxamer 171 Content (μg/mL) =

$$\text{Anti } \log_{10}\left[\frac{\{\log_{10}(SampleArea) - \text{Intercept}\}}{\text{Slope}}\right] \times \text{Dilution Factor}$$

Where Dilution Factor=2/25.

The average of the two preparations will be reported. Report results to two numbers after the decimal place (0.01).

Data Acceptance Criteria

Correlation Between Calibration Standard and Check Standard

The calculated check standard concentration will be compared to the corresponding standard used in the linearity. (The one of the calibration standards, standard 3 is used as check standard).

$$\% \text{ Correlation} = \frac{\text{Concentration of Check Standard}}{\text{Concentration of Check Standard Based on Amount of Standard Weighed}} \times 100$$

Where:

Calculated Check Standard Concentration (μg/mL) =

$$\text{Anti } \log_{10}\left[\frac{\log_{10}(\text{Check Standard Area}) - \text{Intercept}}{\text{Slope}}\right]$$

The correlation between two standards must be between 95% and 105%.

Precision of Sample Replicates

The sample preparation is performed in duplicate; the result for each preparation must agree within ±5% of the average.

Example 2

Determination of Various Non-Ionic Surfactants in Aqueous Solutions

Purpose

This experiment shows that the method used for the determination of Poloxamer 171 in Example 1 above can be used for the analysis of other non-Ionic surfactants.

To perform this study, 5 surfactants were selected. Each surfactant was prepared and injected as Standard at concentration 125 ppm (NB#1703 p. 73). In addition, each surfactant was extracted from solution using the described poloxamer method (NB#2062-35).

Equipment/Materials

| | |
|---|---|
| Triton X-100 | Manufacturer Sigma, Cat #T-9284 |
| Triton X-405 | Manufacturer MP Biomedicals LLC, Cat #152411 |
| Triton BRIJ-35 | Manufacturer ICN Biomedicals Inc, Cat #101111 |
| Tween-20 | Manufacturer Sigma, Cat #P-7949 |
| Tween-80 | Manufacturer TGI America, Cat #T0546 |

Results

The results for this study are presented in Table 1.

TABLE 1

| | Retention Time* | |
|---|---|---|
| Surfactant Name | Standard | Sample |
| Triton X-100 | 3.65 | 3.52 |
| Triton X-405 | 3.31 | 3.31 |
| Triton BRIJ-35 | 4.54 | 4.47 |
| Tween-20 | 3.33 | 3.28 |
| Tween-80 | 9.98 | 9.93 |

*Average of two injections.

Conclusion

Based on the results presented in Table 1, the method used for the determination of Poloxamer 171 in Example 1 can be used for the analysis of other non-ionic surfactants.

What is claimed is:

1. A composition comprising:
   (a) glucose oxidase, wherein the glucose oxidase is present in a concentration of about 90 KU/mL to about 110 KU/mL;
   (b) potassium sorbate, wherein the potassium sorbate is present in a concentration of about 0.12% w/v to about 0.15% w/v; and
   (c) a potassium phosphate buffer; wherein the potassium phosphate buffer is present in a concentration of about 0.01 M.

2. The composition of claim 1, wherein the glucose oxidase is stable for at least 6 months in a plastic container.

3. The composition of claim 1, wherein the glucose oxidase is present in a concentration of about 100 KU/mL.

4. The composition of claim 1, wherein the potassium sorbate is present in a concentration of about 0.15% w/v.

* * * * *